United States Patent
Mohanlal et al.

(10) Patent No.: US 11,400,086 B2
(45) Date of Patent: Aug. 2, 2022

(54) METHOD OF REDUCING CHEMOTHERAPY-INDUCED NEUTROPENIA

(71) Applicant: BEYONDSPRING PHARMACEUTICALS, INC., New York, NY (US)

(72) Inventors: Ramon Mohanlal, New York, NY (US); Lan Huang, New York, NY (US); George Kenneth Lloyd, San Carlos, CA (US)

(73) Assignee: BeyondSpring Pharmaceuticals, Inc., New York, NY (US)

( * ) Notice: Subject to any disclaimer, the term of this patent is extended or adjusted under 35 U.S.C. 154(b) by 0 days.

(21) Appl. No.: 16/482,547

(22) PCT Filed: Feb. 1, 2018

(86) PCT No.: PCT/US2018/016498
§ 371 (c)(1),
(2) Date: Jul. 31, 2019

(87) PCT Pub. No.: WO2018/144764
PCT Pub. Date: Aug. 9, 2018

(65) Prior Publication Data
US 2020/0038395 A1  Feb. 6, 2020

Related U.S. Application Data

(60) Provisional application No. 62/621,533, filed on Jan. 24, 2018, provisional application No. 62/453,375, filed on Feb. 1, 2017.

(51) Int. Cl.
| | |
|---|---|
| *A61K 31/496* | (2006.01) |
| *A61P 37/00* | (2006.01) |
| *A61P 35/00* | (2006.01) |
| *A61K 31/337* | (2006.01) |
| *A61K 38/19* | (2006.01) |

(52) U.S. Cl.
CPC ......... *A61K 31/496* (2013.01); *A61K 31/337* (2013.01); *A61K 38/193* (2013.01); *A61P 35/00* (2018.01); *A61P 37/00* (2018.01)

(58) Field of Classification Search
CPC .. A61K 31/496; A61K 31/337; A61K 38/193; A61P 37/00; A61P 35/00
See application file for complete search history.

(56) References Cited

U.S. PATENT DOCUMENTS

| | | | |
|---|---|---|---|
| 4,535,183 A | 8/1985 | Kneen | |
| 5,607,934 A | 3/1997 | Tone et al. | |
| 5,733,888 A | 3/1998 | Carver et al. | |
| 5,852,018 A | 12/1998 | Bryans et al. | |
| 5,872,151 A | 2/1999 | Rhodes | |
| 5,874,443 A | 2/1999 | Kiely et al. | |
| 5,886,210 A | 3/1999 | Rayle et al. | |
| 5,891,877 A | 4/1999 | Brocchini et al. | |
| 5,922,683 A | 7/1999 | Or et al. | |
| 5,939,098 A | 8/1999 | Reidenberg et al. | |
| 5,958,980 A | 9/1999 | Rhodes | |
| 6,069,146 A | 5/2000 | Fenical et al. | |
| 6,096,786 A | 8/2000 | Rhodes | |
| 6,350,759 B1 | 2/2002 | Casara et al. | |
| 6,358,957 B1 | 3/2002 | Fukumoto et al. | |
| 6,500,825 B2 | 12/2002 | Lan et al. | |
| 6,506,787 B2 | 1/2003 | Fujishita et al. | |
| 6,509,331 B1 | 1/2003 | Audia et al. | |
| 6,583,143 B2 | 6/2003 | Haddach | |
| 6,713,480 B2 | 3/2004 | Fukumoto et al. | |
| 6,808,710 B1 | 10/2004 | Wood et al. | |
| 6,972,289 B1 | 12/2005 | Kanzaki et al. | |
| 7,026,322 B2 | 4/2006 | Hayashi et al. | |
| 7,064,201 B2 | 6/2006 | Hayashi et al. | |
| 7,488,802 B2 | 2/2009 | Collins et al. | |
| 7,629,380 B2 | 12/2009 | McMorris et al. | |
| 7,635,757 B2 | 12/2009 | Freeman et al. | |
| 7,674,903 B2 | 3/2010 | Hayashi et al. | |
| 7,700,615 B2 | 4/2010 | Edwards et al. | |
| 7,919,497 B2 | 4/2011 | Palladino et al. | |
| 7,943,743 B2 | 5/2011 | Korman et al. | |
| 7,956,058 B2 | 6/2011 | Hayashi et al. | |
| 8,008,449 B2 | 8/2011 | Korman et al. | |
| 8,168,757 B2 | 5/2012 | Finnefrock et al. | |
| 8,217,149 B2 | 7/2012 | Irving et al. | |
| 8,247,552 B2 | 8/2012 | Palladino et al. | |

(Continued)

FOREIGN PATENT DOCUMENTS

| | | |
|---|---|---|
| CA | 2 403 790 A1 | 7/2001 |
| EA | 010198 B1 | 6/2008 |

(Continued)

OTHER PUBLICATIONS

Younis et al, "The cost-utility of adjuvant chemotherapy using docetaxel and cyclophosphamide compared with doxorubicin and cyclophosphamide in breast cancer." 2011. Current Oncology, vol. 18, No. 6, pp. e298-e296 (Year: 2011).*

"Highlights of Prescribing Information." [online][Retrieved Apr. 16, 2020 from https://www.accessdata.fda.gov/drugsatfda_docs/label/2015/125031s180lbl.pdf] Rev. Nov. 2015. U.S. Food and Drug Administration. Reference ID: 4192944. (Year: 2015).*

"Definition of 'within'". [Online] [2015 Archived version accessed on Aug. 13, 2020 from https://web.archive.org/web/20151030162428/https://dictionary.cambridge.org/us/dictionary/english/within. Cambridge English Dictionary. (Year: 2015).*

(Continued)

*Primary Examiner* — Elly-Gerald Stoica

(74) *Attorney, Agent, or Firm* — Knobbe, Martens, Olson & Bear, LLP

(57) ABSTRACT

Disclosed herein are plinabulin and the use for reducing neutropenia. Some embodiments relate to reducing the docetaxel induced neutropenia using plinabulin.

19 Claims, 1 Drawing Sheet

(56) References Cited

U.S. PATENT DOCUMENTS

| | | | |
|---|---|---|---|
| 8,618,292 B2 | 12/2013 | Palladino et al. | |
| 9,358,289 B2 | 6/2016 | Korman et al. | |
| 9,394,368 B2 | 7/2016 | Brogdon et al. | |
| 10,076,518 B2 | 9/2018 | Huang | |
| 10,155,748 B2 | 12/2018 | Huang et al. | |
| 10,238,650 B2 | 3/2019 | Huang | |
| 10,550,104 B2 | 2/2020 | Huang et al. | |
| 10,569,169 B2 | 2/2020 | Li et al. | |
| 10,596,169 B2 * | 3/2020 | Huang | A61P 35/00 |
| 10,668,063 B2 | 6/2020 | Huang | |
| 11,045,467 B2 | 6/2021 | Huang | |
| 2002/0028819 A1 | 3/2002 | Teng et al. | |
| 2002/0143021 A1 | 10/2002 | Fukumoto et al. | |
| 2004/0102454 A1 | 5/2004 | Hayashi et al. | |
| 2004/0176372 A1 | 9/2004 | Suto et al. | |
| 2005/0090667 A1 | 4/2005 | Hayashi et al. | |
| 2005/0197344 A1 | 9/2005 | Palladino et al. | |
| 2006/0079534 A1 | 4/2006 | Kanzaki et al. | |
| 2006/0167010 A1 | 7/2006 | Hayashi et al. | |
| 2006/0217553 A1 | 9/2006 | Hayashi et al. | |
| 2006/0223822 A1 | 10/2006 | Hayashi et al. | |
| 2006/0223823 A1 | 10/2006 | Hayashi et al. | |
| 2007/0078138 A1 | 4/2007 | Palladino et al. | |
| 2007/0293453 A1 | 12/2007 | Fisher et al. | |
| 2008/0199485 A1 | 8/2008 | Kundig et al. | |
| 2008/0221122 A1 | 9/2008 | Palladino et al. | |
| 2008/0255035 A1 | 10/2008 | Trieu et al. | |
| 2009/0170837 A1 | 7/2009 | Gourdeau et al. | |
| 2009/0317368 A1 | 12/2009 | Chen | |
| 2012/0041070 A1 | 2/2012 | Shengfan et al. | |
| 2012/0277251 A1 | 11/2012 | Palladino et al. | |
| 2013/0131018 A1 | 5/2013 | Leblond et al. | |
| 2013/0303481 A1 | 11/2013 | Marcus | |
| 2014/0322275 A1 | 10/2014 | Brogdon et al. | |
| 2015/0202291 A1 | 7/2015 | Bosch et al. | |
| 2015/0291549 A1 | 10/2015 | Chupak et al. | |
| 2016/0250209 A1 | 9/2016 | Huang | |
| 2017/0226221 A1 | 8/2017 | Madiyalakan et al. | |
| 2018/0028531 A1 | 2/2018 | Huang et al. | |
| 2018/0036304 A1 | 2/2018 | Huang | |
| 2018/0042921 A1 | 2/2018 | Huang | |
| 2019/0000841 A1 | 1/2019 | Huang | |
| 2019/0175587 A1 | 6/2019 | Huang et al. | |
| 2019/0380983 A1 | 12/2019 | Mohanlal | |
| 2020/0129504 A1 | 4/2020 | Mohanlal et al. | |
| 2020/0237754 A1 | 7/2020 | Huang | |
| 2020/0277280 A1 | 9/2020 | Huang | |
| 2020/0281921 A1 | 9/2020 | Huang | |
| 2021/0030843 A1 | 2/2021 | Mohanlal | |
| 2021/0046068 A1 | 2/2021 | Huang | |
| 2021/0161844 A1 | 6/2021 | Mohanlal et al. | |
| 2021/0161888 A1 | 6/2021 | Huang et al. | |
| 2021/0177952 A1 | 6/2021 | Mohanlal et al. | |
| 2021/0275524 A1 | 9/2021 | Huang | |

FOREIGN PATENT DOCUMENTS

| | | | |
|---|---|---|---|
| EA | 016817 B1 | 7/2012 | |
| EP | 0 054 924 A2 | 6/1982 | |
| EP | 0 655 060 B1 | 1/1998 | |
| EP | 1 264 831 A1 | 12/2002 | |
| GB | 2143823 | 2/1985 | |
| JP | 5009164 | 1/1993 | |
| JP | H05255106 | 10/1993 | |
| JP | 10130266 | 5/1998 | |
| JP | 2002-507612 A | 3/2002 | |
| JP | 2007-520565 A | 7/2007 | |
| JP | 2010-526031 A | 7/2010 | |
| JP | JR 2012-144512 | 8/2012 | |
| JP | 2013-501791 | 1/2013 | |
| JP | 2016-516523 | 6/2016 | |
| JP | 2016-536352 A | 11/2016 | |
| JP | 2018-5201178 A | 7/2018 | |
| JP | 6411523 | 10/2018 | |
| KR | 10-2018-0027563 A | 3/2018 | |
| RU | 2011 148 945 A | 4/2010 | |
| RU | 2662298 C2 | 7/2018 | |
| WO | WO 87/05297 | 9/1987 | |
| WO | WO 94/07479 | 4/1994 | |
| WO | WO 95/06077 A2 | 3/1995 | |
| WO | WO 1995/21832 | 8/1995 | |
| WO | WO 1996/20190 | 7/1996 | |
| WO | WO 1999/38844 | 8/1999 | |
| WO | WO 1999/048889 | 9/1999 | |
| WO | WO 2001/053290 | 7/2001 | |
| WO | WO 2001/070663 A2 | 9/2001 | |
| WO | WO 03/074550 | 9/2003 | |
| WO | WO 03/097164 | 11/2003 | |
| WO | WO 2004/054498 A2 | 7/2004 | |
| WO | WO 2004/054498 A3 | 7/2004 | |
| WO | WO 2004/093831 A2 | 11/2004 | |
| WO | WO 2005/077940 A1 | 8/2005 | |
| WO | WO 2006/121168 A1 | 11/2006 | |
| WO | WO 07035841 | 3/2007 | |
| WO | WO 07/113648 | 10/2007 | |
| WO | WO 2008/128169 A1 | 10/2008 | |
| WO | WO 2009/089260 A2 | 7/2009 | |
| WO | WO 2010/001169 A2 | 1/2010 | |
| WO | WO 10/083439 | 7/2010 | |
| WO | WO 2011/034954 A1 | 3/2011 | |
| WO | WO 11/050344 | 5/2011 | |
| WO | WO 2011/066389 A1 | 6/2011 | |
| WO | WO 2011/079507 A1 | 7/2011 | |
| WO | WO 2011/109625 A1 | 9/2011 | |
| WO | WO 2011/146382 A1 | 11/2011 | |
| WO | WO 2011/151423 A1 | 12/2011 | |
| WO | WO 2012/014549 A1 | 2/2012 | |
| WO | WO 2012/035436 A1 | 3/2012 | |
| WO | WO 12/074904 | 6/2012 | |
| WO | WO 2012/145493 A1 | 10/2012 | |
| WO | WO 2013/078537 A1 | 6/2013 | |
| WO | WO 2013/090552 A1 | 6/2013 | |
| WO | WO 2013/177633 A1 | 12/2013 | |
| WO | WO 2014/066834 A1 | 5/2014 | |
| WO | WO 2014/130657 A1 | 8/2014 | |
| WO | WO 2014/160183 | 10/2014 | |
| WO | WO 2014/195852 A1 | 12/2014 | |
| WO | WO 2015/051543 A1 | 4/2015 | |
| WO | WO-2015051543 A1 * | 4/2015 | A61K 31/337 |
| WO | WO 15/069770 | 5/2015 | |
| WO | WO 15/069790 | 5/2015 | |
| WO | WO 2015/160641 A2 | 10/2015 | |
| WO | WO 2016/130839 A1 | 8/2016 | |
| WO | WO 2016/144635 A1 | 9/2016 | |
| WO | WO 2016/144636 A1 | 9/2016 | |
| WO | WO2016144636 * | 9/2016 | A61K 31/496 |
| WO | WO 16/165007 | 10/2016 | |
| WO | WO 2017/011399 A1 | 1/2017 | |
| WO | WO 17/062505 | 4/2017 | |
| WO | WO 2017/139231 A1 | 8/2017 | |
| WO | WO 2017/214052 A1 | 12/2017 | |
| WO | WO 2018/129381 A1 | 7/2018 | |
| WO | WO 2018/144764 A1 | 8/2018 | |
| WO | WO 2018/169887 A1 | 9/2018 | |

OTHER PUBLICATIONS

Crawford, J. "Once-Per-Cycle Pegfilgrastim (Neulasta) for the Management of Chemotherapy-Induced Neutropenia". Seminars in Oncology, vol. 30, No. 4, Suppl 13 Aug. 2003: pp. 24-30. (Year: 2003).*

Dale, DC. "Neutropenia". Oct. 2015. eLS. John Wiley & Sons, Ltd: Chichester, p. 1-8 (Year: 2015).*

Anonymous, NCT03294577, Sep. 27, 2017. (Year: 2017).*

Abels, Christoph, Targeting of the Vascular System of Solid Tumours by Photodynamic Therapy (PDT), Photochem Photobiol Sci., (Mar. 2004) 3: 765-771.

Abstracts of the 1999 Joint Chubu and Kansai Branch Conference and Symposia of Japan Society for Bioscience, Biotechnology, and Agrochemistry, (1999) p. 48.

Acquaviva et al., "Targeting KRAS-Mutant Non-Small Cell Lung Cancer with the Hsp90 Inhibitor Ganetespib", Mol Cancer Ther, Dec. 2012, 11(12), pp. 2633-2643.

(56) References Cited

OTHER PUBLICATIONS

Agarwal et al., "OP449, a Novel SET Antagonist, Is Cytotoxic to Leukemia Cells and Enhances Efficacy of Tyrosine Kinase Inhibitors in Drug-Resistant Myeloid Leukemias," pursuant to an EMBASE record for a Conference Abstract: 603. Oncogenes and Tumor Suppressors: Poster II (Nov. 15, 2013) Blood (2013) 122(21): 2511.
Aggarwal et al., Antiangiogenic agents in the management of non-small cell lung cancer: Where do we stand now and where are we headed? Cancer Biology & Therapy (2012), 13(5), 247-263.
Ahmed et al. "A new rapid and simple non-radioactive assay to monitor and determine the proliferation of lymphocytes: an alternative to [$^3$ H]thymidine incorporation assay." J. Immunol. Methods. 170, 211-224 (1994).
Akerlund et al., "Diketopiperazine-Based Polymers from Common Amino Acids," Journal of Applied Polymer Science, (2000) 78 (12), 2213-2218.
Algaier et al. "The effects of dimethyl sulfoxide on the kinetics of tubulin assembly." Biochim. Biophys. Acta. 954, 235-43 (1988).
Ali et al. "Toxicity of echinulin from Aspergillus chevalieri in rabbits." Toxicology Letters. (1989) 48: 235-41.
Asahina, T., "Spectrochemical Study of Amino-acid Anhydrides," Bulletin of the Chemical Society of Japan, (1930) 5, 354-365.
Augustin, M. "Die Umsetzung des 2,5-Diketopiperazins mit Aldehyden und Nitrosoverbindungen" Journal für Praktische Chemie, (1966) 32(4), 158-166.
Aviel-Ronen et al., "K-ras Mutations in Non-Small-Cell Lung Carcinoma: A Review," Clinical Lung Cancer (Jul. 2006) vol. 8, No. 1, pp. 30-38.
Bankowska et al., Derivatives of 1,2,3-triazole. Potential drugs?, Wiadomosci Chemiczne (2012), 66(11-12), 993-1022.
Beavis et al., "Dual PD-1 and CTLA-4 Checkpoint Blockade Promotes Antitumor Immune Responses through CD4+Foxp3— Cell-Mediated Modulation of CD103+ Dendritic Cells," Cancer Immunol Res (Sep. 2018) 6(9):1069-1081.
Bergman et al., Ariloxy Substituted N-arylpiperazinones as Dual Inhibitors of Farnesyltransferase and Geranylgeranyltransferase-1, Bioorg & Med Chem Lttrs. (Mar. 2001) 11: 1411-1415.
Bertelsen et al., "Vascular effects of plinabulin (NPI-2358) and the influence on tumour response when given alone or combined with radiation," International Journal of Radiation Biology (2011),87(11), 1126-1134.
Bertino.J., et al., "Principles of Cancer Therapy." Cecil Textbook of Medicine. Eds. Lee Goldman, et al. 21nd ed., (2000), Chapter 198, pp. 1060-1074.
Blayney et al., "Plinabulin, a Novel Small Molecule That Ameliorates Chemotherapy-Induced Neutropenia, Is Administered on the Same Day of Chemotherapy and Has Anticancer Efficacy", Meeting Info.: 58th Annual Meeting and Exposition of the American Society-of-Hematology (ASH), Blood (2016) 128(22): 2508 Abstract.
Bond et al. "The Synthesis of Viridamine, a Penicillium Viridicatum Mycotoxin." Synthetic Commun. 19 (13&14), 2551-2566 (1989).
Borisy, G.G. "A Rapid Method for Quantitative Determination of Microtubule Protein using DEAE-Cellulose Filters." Anal. Biochem. 50, 373-385(1972).
Brahmer et al., "Safety and Activity of Anti-PD-L1 Antibody in Patients with Advanced Cancer," N Engl J Med (2012) 366:2455-2465.
Burtles, Sally, "Transition from Preclinical to first-in-man Phase", Expert Scientific Group on Phase One Clinical Trials Final Report, Presentation Jun. 19, 2006, pp. 35-38.
Cai, Sui X., "Small Molecule Vascular Disrupting Agents: Potential New Drugs for Cancer Treatment", Recent Pat Anticancer Drug Discov. (2007) 2(1): 79-101.
Cai, Small molecule vascular disrupting agents: potential new drugs for cancer treatment, a 2009 update, Frontiers in Anti-Cancer Drug Discovery (2010), 1, 380-427.
Callahan et al., "At the Bedside: CTLA-4- and PD-1-blocking antibodies in cancer immunotherapy", J Leukocyte Biol, vol. 94, Jul. 2013, pp. 41-53.

Chaplin et al., "Antivascular approaches to solid tumour thereapy: evaluation of tubulin binding agents", Br. J. Cancer 1996, 74 (Suppl. XXVII), S86-S88.
Chen et al., "Adjuvant effect of docetaxel on the immune responses to influenza A H1N1 vaccine in mice," BMC Immunology (2012) 13:36, pp. 1-12.
Chin et al., "Immune Intervention with Monoclonal Antibodies Targeting CD152 (CTLA-4) for Autoimmune and Malignant Diseases," Chang Gung Med J (Jan.-Feb. 2008) vol. 31, No. 1, pp. 1-15.
ClinicalTrials.gov Identifier NCT00892931, "Phase 2 study MPC-6827 for recurrent glioblastoma multiforme," (Oct. 14, 2011). [retrieved from internet on Jul. 30, 2019] <URL: https://clinicaltrials.gov/ct2/show/NCT00892931> 7 pages.
ClinicalTrials.gov Identifier NCT02846792, "Nivolumab and Plinabulin in Treating Patients With Stage IIIB-IV, Recurrent, or Metastatic Non-small Cell Lung Cancer," (Jul. 27, 2016). [retrieved from internet on Sep. 17, 2019], <URL: https://clinicaltrials.gov/ct2/show/NCT02846792?term=plinabuilin&rank=1> 11 pages.
Cole, P., "DURVALUMAB, Human anti-PD-L1 monoclonal antibody Immune checkpoint inhibitor Oncolytic", Drugs of the Future 2014, 39(12): pp. 843-847.
Cooper et al., "Response to BRAF Inhibition in Melanoma Is Enhanced When Combined with Immune Checkpoint Blockade," Published OnlineFirst Apr. 29, 2014; DOI: 10.1158/2326-6066.CIR-13-0215; Cancer Immunol Res (Jul. 2014) 2(7) 643-654.
Costa et al., "Analyses of selected safety endpoints in phase 1 and late-phase clinical trials of anti-PD-1 and PD-L1 inhibitors: prediction of immune-related toxicities," Oncotarget (2017) vol. 8, No. 40, pp. 67782-67789.
Cui et al. "Novel Mammalian Cell Cycle Inhibitors, Tryprostatins A, B and Other Diketopiperazines Produced by Aspergillus fumigatus." J. Antibiotics. 49(6): 527-33 (1996).
Cui et al. "Novel Mammalian Cell Cycle Inhibitors, Tryprostatins A, B and Other Diketopiperazines Produced by Aspergillus fumigatus." J. Antibiotics. 49(6), 534-40 (1996).
Dandan et al., JP 5009164,_Chemical Abstract 119: 8514 (1993).
Davis et al., ZD6126: A Novel Vascular-targeting Agent That Causes Selective Destruction of Tumor Vasculature, Cancer Research (Dec. 15, 2002) 62: 7247-7253.
Dörwald, F., "Side Reactions in Organic Synthesis" Wiley-VCH Verlag GmbH & Co. KgaA, Weinheim, (2005), book cover and preface p. IX only.
Drug Approval and Licensing Procedures in Japan 2001, 2001, pp. 243-244.
Ferrer et al., Plinabulin: tubulin polymerization inhibitor vascular-disrupting agent oncolytic, Drugs of the Future (2010), 35(1), 11-15.
Folkes et al., Synthesis and In Vitro Evaluation of a Series of Diketopiperazine Inhibitors of Plasminogen Activator Inhibitor-1, Bioorg & Med Chem Lttrs., (Jul. 2001) 11: 2589-2592.
Frost et al., Novel Syngeneic Pseudo-orthotopic Prostate Cancer Model: Vascular, Mitotic and Apoptotic Responses to Castration, Microvasc Research (Dec. 2004) 69: 1-9.
Fukushima et al., "Biological Activities of Albonoursin," J. Antibiotics, (1973) 26:175.
Gallina et al., "Condensation of 1,4-diacetylpiperazine-2,5-dione with aldehydes", Tetrahedron 1974, 30, 667-673.
Gameiro et al., "Exploitation of differential homeostatic proliferation of T-cell subsets following chemotherapy to enhance the efficacy of vaccine-mediated antitumor responses," Cancer Immunology Immunotherapy (2011) vol. 60, No. 9, pp. 1227-1242.
Garris et al., "Successful Anti-PD-1 Cancer Immunotherapy Requires T Cell-Dendritic Cell Crosstalk Involving the Cytokines IFN-( and IL-12," Immunity (Dec. 18, 2018) 49, pp. 1-14, e1-e7 (22 pages).
Goldani et al. "Treatment of murine pulmonary mucormycosis with SCH 42427, a broad-spectrum triazole antifungal drug", Correspondence, J Antimicrob Chemother. 33, 369-372 (1994).
Goldfarb et al., "Synthesis of β-2-thienylalanine," Izvestiya Akademii Nauk SSSR, Seriya Khimicheskaya, (1958) 98-100, as abstracted by CAPLUS.
Gordon et al. "Reductive Alkylation on a Solid Phase: Synthesis of a Piperazinedione Combinatorial Library." J. Bioorg. Med. Chem. Letters. 5, 47-50(1995).

(56) References Cited

OTHER PUBLICATIONS

Granville et al., Release of Cytochrome c1 Bax Migration, Bid Cleavage, and Activation of Caspases 2, 3, 6, 7, 8, and 9 during Endothelial Cell Apoptosis, Am J Path., (Oct. 1999) 155(4): 1021-1025.
Gridelli et al., Vascular disrupting agents: a novel mechanism of action in the battle against non-small cell lung cancer, Oncologist (2009), 14(6), 612-620.
Gura, Trisha, "Cancer Models: Systems for Identifying New Drugs are Often Faulty", Science 7(Nov. 1997) 2/8(5340): 1041-1042.
Hamel, E. "Antimitotic Natural Products and Their Interactions with Tubulin." Med. Res. Rev. (1996) 16(2): 207-31.
Hartwell et al. "Checkpoints: Controls that Ensure the Order of Cell Cycle Events." Science. 246, 629-34 (1989).
Hayakawa, Structure-activity relationship analysis, Gan to Kagaku Ryoho (2004), 31(4), 526-528.
Hayashi et al., "Total Synthesis of Anti-microtubule Diketopiperazine Derivatives: Phenylahistin and Aurantiamine," J. Org. Chem., (2000) 65: 8402-8405.
Hayashi et al., Small peptide-based medicinal chemistry for intractable disease, Peptide Science (2009), Volume Date 2008, 45th, 139-140.
Hayashi et al., Medicinal chemistry and chemical biology of diketopiperazine-type antimicrotubule and vascular-disrupting agents, Chemical & Pharmaceutical Bulletin (2013), 61(9), 889-901.
He et al., "Low-dose paclitaxel enhances the anti-tumor efficacy of GM-CSF surface-modified whole-tumor-cell vaccine in mouse model of prostate cancer," Cancer Immunology Immunotherapy (2011) vol. 60, No. 5, pp. 715-730. Abstract.
Heist et al., "Abstract C30: Phase 1/2 study of the vascular disrupting agent (VCA) plinabulin (NPI-2358) combined with docetaxel in patients with non-small cell lung cancer (NSCLC)," Mol. Cancer Ther., 2009; 8(12 Suppl):C30, 2 pages.
Heist et al., "Randomized phase 2 trial of plinabulin (NPI-2358) plus docetaxel in patients with advanced non-small cell lung cancer (NSCLC)." J. Clin. Oncol. (2014) vol. 32, No. 5s, (suppl; abstr 8054).
Heist et al., "Randomized Phase 2 Trial of Plinabulin (NPI-2358) Plus Docetaxel in Patients with Advanced Non-Small Lung Cancer (NSCLC)," 2014 ASCO Annual Meeting . . . (abstr 8054) Poster Presentation. Retrieved from the internet Jul. 17, 2017: <http://meetinglibrary.asco.org/record/92548/poster>.
Helleman et al. "The International Journal of Biochemistry & Cell Biology," vol. 42, pp. 25-30 (2010).
Horak et al. "Structures of the Austalides A-E, Five Novel Toxic Metabolites from Aspergillus ustus." J Chem Soc Chem Commun. (1981) 1265-67.
http://scienceandresearch.homeoffice.gov.uk/animal-research/publications-and-reference/001-abstracts/abstracts2-2006/02november-2006/457?view=Html; "Abstract #457, Animals in Scientific Procedures (2006)"; (accessed on Nov. 19, 2008).
Hyun et al., "Valine dehydrogenase from Streptomyces albus: gene cloning, heterologous expression and identification of active site by site-directed mutagenesis," FEMS Microbiology Letters (Jan. 1, 2000) 182: 29-34.
Iwasaki, S. "Antimitotic Agents: Chemistry and Recognition of Tubulin Molecule." Med Res Rev. (1993) 13: 183-198.
Iwasaki, S. "Bioactive Natural Products Interfering with Microtubule Function." Kagaku to Seibutsu. 32(3): 153-159 (1994).
Ji et al., Tubulin Colchicine Binding Site Inhibitors as Vascular Disrupting Agents in Clinical Developments, Current Medicinal Chemistry (2015), 22(11), 1348-1360.
Jiang et al., "A Novel Peptide Isolated from a Phage Display Peptide Library with Trastuzumab Can Mimic Antigen Epitope of HER-2*," (Feb. 11, 2005) J Biol Chem, vol. 280, No. 6, pp. 4656-4662.
Johnson et al. "Kinetic Analysis of Microtubule Self-assembly in Vitro." J. Mol. Biol. 117, 1-31 (1977).
Jure-Kunkel M. et al., "Synergy between chemotherapeutic agents and CTLA-4 blockade in preclinical tumor models", Cancer Immunol. Immunother. 2013, vol. 62, pp. 1533-1545.
Kamb, Alexander, "What's wrong with our cancer models?", Nature Reviews Drug Discovery (Feb. 2005) 4: 161-165.
Kanoh et al., "(−)-Phenylahistin: A New Mammalian Cell Cycle Inhibitor Produced by Aspergillus USTUS," Bioorganic & Medicinal Chemistry Letters, (1997) 7: 2847-2852.
Kanoh et al., "(−)-Phenylahistin Arrests Cells in Mitosis by Inhibiting Tubulin Polymerization," The Journal of Antibiotics, (1999) 52: 134-141.
Kanoh et al., "Antitumor Activity of Phenylahistin in Vitro and in Vivo," Bioscience Biotechnology Biochemistry, (1999) 63(6): 1130-1133.
Kanoh et al., "Synthesis and Biological Activities of Phenylahistin Derivatives," Bioorganic & Medicinal Chemistry, (1999) 7: 1451-1457.
Kanthou et al., Microtubule depolymerizing vascular disrupting agents: novel therapeutic agents for oncology and other pathologies, International Journal of Experimental Pathology(2009), 90(3), 284-294.
Kanzaki et al., "Enzymatic Synthesis of Physiologically Active Substances Utilizing a Novel System for the Synthesis of Diketopiperazines Comprising Dehydroamino Acids as Constituents," Abstracts of Papers Presented at the 1999 Meeting of the Society for Actinomycetes Japan, (1999) 42 (Abstract Only).
Kanzaki et al., "Novel Cyclic Dipeptide Dehydrogenase and Assay Method for Its Activity," Scientific Reports of the Faculty of Agriculture, Okayama University, (1999) 88: 7-11.
Kanzaki et al., "Enzymatic dehydrogenation of cyclo(L-Phe-L-Leu) to a bioactive derivative, albonoursin," Journal of Molecular Catalysis B: Enzymatic (1999) 6(3): 265-270.
Kanzaki et al., "Effective Production of Dehydro Cyclic Dipeptide Albonoursin Exhibiting Pronuclear Fusion Inhibitory Activity, II. Biosynthetic and Bioconversion Studies," The Journal of Antibiotics, (2000) 53(1): 58-62.
Kanzaki et al., A Novel Potent Cell Cycle Inhibitor Dehydrophenylahistin-Enzymatic Synthesis and Inhibitory Activity toward Sea Urchin Embryo, The Journal of Antibiotics, (Dec. 2002) 55(12): 1042-1047.
Keepers et al. "Comparison of the Sulforhodamine B Protein and Tetrazolium (MTT) Assays for in vitro Chemosensitivity Testing." Eur. J. Cancer. 27, 897-900 (1991).
Kim et al. "Polymer attached cyclic peptides, tetrahedron: Asymmetry." 3(11):1421-1430 (1992).
Kingston, Tubulin-Interactive Natural Products as Anticancer Agents, Journal of Natural Products (2009), 72(3), 507-515.
Kingston, Correction to Tubulin-interactive natural products as anticancer agents, Journal of Natural Products (2011), 74(5), 1352.
Kobayashi et al., "Microtubule Assembly Regulators of Microbial Origin," Abstract of Paper Read at the 1989 Symposium on the Chemistry of Natural Products, (1989) 51.
Kola et al., "Can the pharmaceutical industry reduce attrition rates?", Nature Reviews Drug Discovery (2004) 3: 711-715.
Kondoh et al. "Effects of Tryprostatin Derivatives on Microtubule Assembly In Viro and In Situ." J. Antibiotics. 51, 801-04 (1998).
Kopple et al., "A Convenient Synthesis of 2,5-Piperazinediones1a," The Journal of Organic Chemistry, (1967) 33: 862-864.
Kreamer K., "Immune checkpoint blockade: A New Paradigm in Treating Advanced Cancer", J. Adv. Pract. Oncol., 2014, vol. 5, pp. 418-431.
Krishan, A. "Rapid Flow Cytofluorometric Analysis of Mammalian Cell Cycle by Propidium Iodide Staining." J. Cell Biol. 66, 188-193 (1975).
Kupchan et al. "Steganacin and Steganangin, Novel Antileukemic Lignan Lactones from Steganotaenia araliacea 1-3." J. Am. Chem. Soc. (1973) 95(4): 1335-36.
Küster & Koeppenhöfer, "Über eininge Pyrrolderivate," Z. Physiol, Chem., (1927) 172:126-137.
Lacey et al. "Interaction of Phomopsin A and Related Compounds with Purified Sheep Brain Tubulin." Biochem. Pharmacol. 36, 2133-38 (1987).
Laemmli, U.K. "Cleavage of Structural Proteins during the Assembly of the Head of Bacteriophage T4." Nature. 227, 680-85 (1970).

(56) References Cited

OTHER PUBLICATIONS

Larsen et al. "Aurantiamine, A Kiketopiperazine from Two Varieties of Penicillium Aurantiogriseum." Phytochemistry. 31, 1613-1615 (1992).
Leaf, Clifton, "Why are we losing the war on cancer (And how to win it)?", Health Administrator (2005) XVII(1): 172-183.
Lee et al. "The Reconstitution of Microtubules from Purified Calf Brain Tubulin." Biochemistr. 14(23), 5183-87 (1975).
Lee et al., Colchicine site inhibitors of microtubule integrity as vascular disrupting agents, Drug Development Research (2008), 69(6), 352-358.
Li, Y., et al. "Interaction of marine toxin dolastatin 10 with porcine brain tubulin: competitive inhibition of rhizoxin and phomopsin A binding." Chem. Biol. Interact. 93, 175-83 (1994).
Liao et al., "Design and synthesis of novel soluble 2,5-diketopiperazine derivatives as potential anticancer agents," European J Med Chem (2014) 83:236-244.
Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) 21(7) 1639-1651.
Liwo et al. "Origin of the Ring-Ring Interaction in Cyclic Dipeptides Incorporating an Aromatic Amino Acid." Tetrahedron Lett. 26, 1873-1876 (1985).
Lloyd et al., Abstract A07: Plinabulin: Evidence for an immune-mediated mechanism of action, In: Proceedings of the AACR Special Conference: Function of Tumor Microenvironment in Cancer Progression; Jan. 7-10, 2016; San Diego, CA. Philadelphia (PA): AACR; Cancer Research. Aug. 2016. 76(15 Supp.): abstract nr A07.
Luduena, R.F. "Contrasting Roles of Tau and Microtubule-associated Protein 2 in the Vinblastine-induced Aggregation of Brain Tubulin." J. Biol. Chem. 259:12890-98 (1984).
Lyman et al., "Risk Models for Predicting Chemotherapy-Induced Neutropenia," The Oncologist (2005) 10:427-437.
Lynch et al., "Ipilimumab in Combination With Paclitaxel and Carboplatin as First-Line Treatment in Stage IIIB/IV Non-Small-Cell Lung Cancer: Results From a Randomized, Double-Blind, Multicenter Phase II Study," (Jun. 10, 2012) J Clin Oncol, vol. 30, No. 17, pp. 2046-2054.
Mahindroo et al., "Antitubulin Agents for the Treatment of Cancer—A Medicinal Chemistry Update", Expert Opin. Ther. Patents (2006) 16(5): 647-691.
Mahoney et al., "The Next Immune-Checkpoint Inhibitors: PD-1/PD-L1 Blockade in Melanoma," Clinical Therapeutics (Apr. 2015) vol. 37, Issue 4, pp. 764-782. Abstract.
Matsuda et al., "Pilot study of WT1 peptide-pulsed dendritic cell vaccination with docetaxel in esophageal cancer," Oncology Letters (Jul. 2018) vol. 16, No. 1, pp. 1348-1356.
Millward et al., "Phase I trial of NPI-2358 (a novel vascular disrupting agent) plus docetaxel," J. Clin. Oncol. (May 2009) 27(15S): 3571-3571, Abstract.
Millward et al., "Phase 1 study of the novel vascular disrupting agent plinabulin (NPI-2358) and docetaxel," The Journal of New Anticancer Agents, vol. 3, No. 30, Feb. 16, 2011 plinabulin (NPI-2358) and docetaxel, Investigational New Drugs (2012), 30(3), 1065-1073.
Mita et al., "Phase 1 First-in-Human Trial of the Vascular Disrupting Agent Plinabulin (NPI-2358) in Patients with Solid Tumors or Lymphomas," Clinical Cancer Research (2010), 16(23), 5892-5899.
Mita et al., Randomized Phase 2 Study of Docetaxel +/− Plinabulin (NPI-2358) in Patients with Non-Small Cell Lung Cancer (NSCLC), Poster Presentation at ACS Annual '10 Meeting (Jun. 4-8, 2010) 1 page.
Mita et al., "Phase II study of docetaxel with or without plinabulin (NPI-2358) in patients with non-small cell lung cancer (NSCLC)", J. Clin. Oncol., 2010, vol. 28, No. 15 supplement. Abstract 7592, 2 pages.
Mitsudomi et al., "Mutations of ras genes distinguish a subset of non-small-cell lung cancer cell lines from small-cell lung cancer cell lines," Oncogene (Aug. 1991) vol. 6, No. 8, pp. 1352-1362.
Mohanlal et al., "The plinabulin/docetaxel combination to mitigate the known safety concerns of docetaxel," J Clin Oncol (2016) 34(15_suppl), Abstract e20595.
Muguruma et al., OP-20: "Application of Fc-selective Z33-peptide to the preparation of non-covalent-type antibody-antimocrotubule plinabulin conjugate," 34th European Peptide Symposium 2016 & 8th International Peptide Symposium, Journal of Peptide Sci (Sep. 5, 2016—5:30pm)22 Supplement 2 ISSN: 1099-1387 [n English (Oral Presentation). Abstract.
Nagaria et al., "Flavopiridol Synergizes with Sorafenib to Induce Cytotoxicity and Potentiate Antitumorigenic Activity in EGFR/HER02 and Mutant RAS/RAF Breast Cancer Model Systems," NEOPLASIA (Aug. 2013) vol. 15, No. 8, pp. 939-951.
Neidle, Stephen, ed., Cancer Drug Design and Discovery , 9th Edition, Elsevier/Academic Press, (2008) Chapter 18, pp. 427-431.
Nema et al., Excipients and Their Role in Approved Injectable Products: Current Usage and Future Directions, PDA J Pharm Sci and Tech 2011, 65 287-332.
Neuteboom et al., "450 Poster NPI-2358, a novel tumor vascular disrupting agent potentiates the anti-tumor activity of docetaxel in the non small cell lung cancer model MV522," EJC Supplements (2008) 6(12):141.
Nicholson et al., NPI-2358 is a tubulin-depolymerizing agent: in-vitro evidence for activity as a tumor vascular-disrupting agent, Anti-Cancer Drugs (2005), Volume Date 2006, 17(1), 25-31.
Niemann et al, "The Synthesis of the Three Isomeric dl-β-Pyridylalanines" Journal of the American Chemical Society, (1942) 64(7):1678-1682.
Nihei et al., "Evaluation of antivascular and antimitotic effects of tubulin binding agents in solid tumor therapy", Jpn. J. Cancer. Res. 1999, 90, 1387-1395.
Nitecki et al., "A Simple Route to Sterically Pure Diketopiperazines1," The Journal of Organic Chemistry, (1968) 33:864-866.
Ott et al., "CTLA-4 and PD-1/PD-L1 Blockade: New Immunotherapeutic Modalities with Durable Clinical Benefit in Melanoma Patients," Clin. Cancer Res. (Oct. 1, 2013) 19(19):5300-5309.
Pardoll et al., "The blockade of immune checkpoints in cancer immunotherapy," Nat Rev Cancer (May 4, 2016) 12(4): 252-264.
Pattingre et al., "Amino Acids Interfere with the ERK1/2-dependent Control of Macroautophagy by Controlling the Activation of Raf-1 in Human Colon Cancer HT-29 Cells," J Biol Chem (May 9, 2003) vol. 278, No. 19, pp. 16667-16674.
Perez, Edith A., "Paclitaxel in Breast Cancer," The Oncologist, 1998, vol. 3, pp. 373-389.
Petrillo et al., Novel VEGF-independent strategies targeting tumor vasculature: clinical aspects, Current Pharmaceutical Design (2012), 18(19), 2702-2712.
Pettit et al. "Antineoplastic Agents. 291. Isolation and Synthesis of Combretastatins A-4, A-5, and A-6 1a." J. Med. Chem. (1995) 38: 1666-1672.
Prior et al., "A Comprehensive Survey of Ras Mutations in Cancer" Cancer Res. (2012) vol. 72, No. 10, pp. 24570-2467.
Reck, M., "What future opportunities may immuno-oncology provide for improving the treatment of patients with lung cancer?" (2012) Annals of Oncology (Sep. 2012) 23 (Supp. 8) viii28-viii34.
Rhodes, John, "Section Review: Biologicals & Immunologicals: Therapeutic potential of Schiff base-forming drugs," Expert Opinion on Investigational Drugs (1996) vol. 5, Issue 3, pp. 257-268.
Riemer et al., "Matching of trastuzumab (Herceptin®) epitope mimics onto the surface of Her-2/neu—a new method of epitope definition," Mol Immunol 42 (2005) pp. 1121-1124.
Roberge et al., "Antitumor Drug Fostriecin Inhibits the Mitotic Entry Checkpoint and Protein Phospatases 1 and 2A." Cancer Res. 54, 6115-21 (1994).
Roberts et al, "Trends in the Risks and Benefits to Patients with Cancer Participating in Phase 12 Clinical Trials", JAMA (2004) 292(17): 2130-2140.
Rowinsky et al. "Taxol: A Novel Investigational Antimicrotubule Agent." J. Natl. Cancer Inst. 82(15): 1247-59 (1990).
Rowinsky et al, "The clinical pharmacology and use of antimicrotubule agents in cancer chemotherapeutics", Pharmacol. Ther. 1991, 52, 35-84.

(56) References Cited

OTHER PUBLICATIONS

Rozali et al., "Programmed Death Ligand 2 in Cancer-Induced Immune Suppression," Clinical and Developmental Immunology (2012) Article ID 656340, pp. 1-8.

Sackett, D.L. "Podophyllotoxin, Steganacin and Combretastatin: Natural Products that Bind at the Colchicine Site of Tubulin." Pharmacol. Ther. (1993) 59: 163-228.

Saito et al., "Synthesis of novel octahydro-1, 5-imino-3-benzazocin-4, 7, 10-trione derivatives having a methyl group at the C-2 position as ABC ring models of saframycins," Chemical & Pharmaceutical Bulletin (1997) 45(7):1120-1129.

Scholl et al., "Synthetic Lethal Interaction between Oncogenic KRAS Dependency and the STK33 Suppression in Human Cancer Cells", Cell (May 29, 2009) 137 pp. 821-834.

Sezaki et al., "Drug Delivery Systems", Drug Development, (Jul. 1989) 13: 116, Table 2. 29.

Shen et al., NPI-2358 rapidly inhibit blood flow in tumor treatment by analyzing dynamic contrast enhanced magnetic resonance imaging parameters, Zhonghua Zhongliu Fangzhi Zazhi (2010), 17(7),488-490, 494.

Shen et al., Time- and dose-dependent vascular changes induced by the novel vascular disrupting drug NPI-2358 in a murine cancer model monitored with DCE-MRI, U.S. Chinese Journal of Lymphology and Qncology(2010), 9(4), 151-153.

Sherline et al. "Binding of Colchicine to Purifiied Microtubule Protein." J. Biol. Chem. 250, 5481-86 (1975).

Shi, Q et al, "Recent progress in the development of tubulin inhibitors as antimitotic antitumor agents", Curr. Pharm. Des. 1998, 4, 219-248.

Singh et al., "A novel vascular disrupting agent plinabulin triggers JNK-mediated apoptosis and inhibits angiogenesis in multiple myeloma cells," Blood (2011), 117(21), 5692-5700.

Siwicka et al., "Diastereodivergent Synthesis of 2,5-diketopiperazine Derivatives of Beta-Carboline and Isoquinoline from L-amino Acids," Tetrahedron: Asymmetry (Mar. 7, 2005) 16(5): 975-993.

Smedsgaard et al. "Using direct electrospray mass spectrometry in taxonomy and secondary metabolite profiling of crude fungal extracts." J. Microbiol. Meth. (1996) 25: 5-17.

Sölter et al., Barettin, Revisited? Tetrahed Lttrs. (Mar. 2002) 43: 3385-3386.

Spear et al., Vascular disrupting agents (VDA) in oncology: advancing towards new therapeutic paradigms in the clinic, Current Drug Targets (2011), 12(14), 2009-2015.

Stein, J., ed. "Internal Medicine," Fourth Edition, Mosby-Year Book, Inc., (1994), Chapters 71-72, pp. 699-729.

Stenehjem et al., "PDI/PDLI inhibitors for the treatment of advanced urothelial bladder cancer," OncoTargets and Therapy (2018) 11:5973-5989.

Steyn, P.S. "The Structures of Five Diketopiperazines from Aspergillus Ustus." Tetrahedron. 29, 107-120 (1973).

Sugar et al. "Comparison of Three Methods of Antifungal Susceptibility Testing with the Proposed NCCLS Standard Broth Macrodilution Assay: Lack of Effect of Phenol Red." Diagn Micro and Infect Diseases. 21, 129-133 (1995).

Takahashi et al. "Rhizoxin binding to tubulin at the maytansine-binding site." Biochim. Biophys. Acta. 926, 215-23 (1987).

Talmadge et al., Murine models to evaluate novel and conventional therapeutic strategies for cancer., Am J Pathol, 2007, vol. 170, Issue 3, pp. 793-804.

Thorpe, Philip E., "Vascular Targeting Agents as Cancer Therapeutics," Clinical Cancer Research, vol. 10, 415-427, Jan. 15, 2004.

Tiwari et al. "A pH- and Temperature-Dependent Cycling Method that doubles the Yield of Microtubule Protein." Anal. Biochem. 215, 96-103 (1993).

Topalian et al., "Safety, Activity, and Immune Correlates of Anti-PD-1 Antibody in Cancer," N Engl J Med. (Jun. 28, 2012) 366(26):2443-2454.

Tozer et al., Tumour vascular disrupting agents: combating treatment Resistance, British Journal of Radiology (2008), 81(Spec. Iss. 1), S12-S20.

Turner et al. "Recent Advances in the Medicinal Chemistry of Antifungal Agents." Current Pharmaceutical Design. 2, 209-224 (1996).

University of Washington, "Nivolumab and Plinabuilin in Treating Patients With Stage IIIB-IV, Recurrent, or Metastatic Non-small Cell Lung Cancer," Clinical trial study first posted Jul. 27, 2016. URL:https://clinicaltrials.gov/ct2/show/NCT02846792.

Usui et al. "Tryprostatin A, a specific and novel inhibitor of microtubule assembly." Biochem J. 333, 543-48 (1998).

Van der Waerden, B.L., "Wirksamkeits- und Konzentrationsbestimmung durch Tierversuche." Arch Exp Pathol Pharmakol. 195, 389-412, (1940).

Verdier-Pinard et al., "Structure-Activity Analysis of the Interaction of Curacin A, the Potent Colchicine Site Antimitotic Agent, with Tubulin and Effects of Analogs on the Growth of MCF-7 breast Cancer Cells." Mol. Pharmacol., 53, 62-76 (1998).

Voskoglou-Nomikos et al., Clinical predictive value of the in vitro cell line, human xenograft, and mouse allograft preclinical cancer models, National Cancer Institute of Canada Clinical Trials Group et al., 2003, vol. 9, pp. 4227-4239.

Wang, T. et al. 1998 "Microtubule interfering agents activate c-Jun N-terminal kinase/stress-activated protein kinase through both Ras and apoptosis signal-regulating kinase pathways". J Biol Chem. vol. 273, No. 9, pp. 4928-4936.

Wang, Y. et al, "Structures of a diverse set of colchicine binding site inhibitors in complex with tubulin provide a rationale for drug discovery." FEBS Journal (2016) 283, 102-111.

Weisenberg et al. "The Colchicine-Binding Protein of Mammalian Brain and its Relation to Microtubules." Biochemistry (1968) 7(12): 4466-79.

Wilt et al. "Anal cancer in Alaska; a retrospective study of incidence, treatment, and outcomes". Alaska Med Jul.-Sep. 2002; 44(3):56-9, 62.

Yahara et al. "Microtubule Organization of Lymphocytes and its Modulation by Patch and Cap Formation." Cell. 15, 251-259 (1978).

Yamazaki et al. "Crystal Structure and Absolute Configuration of Fumitremorgin B, a Tremorgenic Toxin from Aspergillus Fumigatus Fres." Tetrahedron Lett. 1, 27-28 (1975).

Yamazaki et al. "Synthesis and Structure-Activity Relationship Study of Antimicrotubule Agents Phenylahistin Derivatives and a Didehydropiperazine-2,5-dione Structure", Journal of Medicinal Chemistry, 2012, vol. 55, No. 3, pp. 1056-1071.

Yamazaki et al., Drug discovery study on cyclic dipeptides anti-cancer drugs and chemical biological development, Idenshi Igaku Mook (2012), 21(Saishin Pepuchido Gosei Gijutsu to Sono Soyaku Kenkyu eno Oyo), 260-266.

Yamori T., "A Human Cell Line Panel for Screening Anti-Cancer Drugs", Jap. J. Cancer Chemother. 24, 129-35 (1997).

Yang et al., "The KRAS Mutation is Highly Correlated With EGFR Alterations in Patients With Non-small Cell Lung Cancer," Fooyin J Health Sci (2009) vol. 1(2): pp. 65-71.

Yeh et al., "A Phase 1 Trial Combining Plinabulin and Nivolumab for Metastatic Squamous NSCLC," International Association for the Study of Lung Cancer, Journal of Thoracic Oncology (Sep. 6, 2015) Abstract 602, p. 2.01-087.

Yin et al., "Human Mutations That Confer Paclitaxel Resistance," Mol. Cancer Ther. vol. 9(2), pp. 327-335 (2010).

Yokoi et al, "Neihumicin, A New Cytotoxic Antibiotic From Micromonospora Neihuensis," The Journal of Antibiotics, (Apr. 1988) 41(4):494-501.

Yoshida, M.M. Protein Nucleic Acid Enzymes. 38, 1753-1765 (1993).

Yoshimatsu et al. "Mechanism of Action of E7010, an Orally Active Sulfonamide Antitumor Agent: Inhibition of Mitosis by Binding to the Colchicine Site of Tubulin." Cancer Res. 57, 3208-13 (1997).

Zawadzka et al., "Diastereoselective Synthesis of 1-Benzyltetrahydroisoquinoline Derivatives from Amino Acids by 1,4 Chirality Transfer", Euro J Org Chem., (Jul. 2003) 2003(13): 2443-2453.

Zheng, Lei, "Does vaccine-primed pancreatic cancer offer better candidates for immune-based therapies?" Immunotherapy (2014) 6(10):1017-1020.

(56) References Cited

OTHER PUBLICATIONS

Zou et al., Effect of Interleukin-1 Blockers, CK112, and CK116 on Rat Experimental Choroidal Neovascularization In Vivo and Endothelial Cell Cultures In Vitro, J Ocul Pharma Thera., (2006) 22(1): 19-25.
International Search Report and Written Opinion dated May 8, 2018 for PCT/US2018/016498.
International Preliminary Examination Report dated Aug. 15, 2019 for PCT/US2018/016498.
Abolhasani et al., Jan. 2015, In-silico investigation of tubulin binding modes of a series of novel antiproliferative spiroisoxazoline compounds using docking studies, Iranian Journal of Pharmaceutical Research, 14(1):141-147.
Braga et al. "Crystal Polymorphism and Multiple Crystal Forms," Struct Bond (2009) 132:25-50.
Caira, 1998, Crystalline polymorphism of organic compounds, Topics in Current Chemistry, 198:163-208.
Carter et al., "No patient left behind: The promise of immune priming with epigenetic agents," Oncoimmunology (2017) vol. 6, No. 10, e1315486 (13 pages).
Dunitz et al., "Disappearing Polymorphs," Acc. Chem. Res. (1995) vol. 28, No. 4, pp. 193-200.
Fernandez-Medarde et al., Mar. 2011, Ras in cancer and developmental diseases, Genes & Cancer, 2(3):344-358.
Field et al., 2014, Microtubule-targeting agents are clinically successful due to both mitotic and interphase impairment of microtubule function, Bioorganic & Medicinal Chemistry, 22:5050-5059.
Gu et al., "Identification of CTLA-4 isoforms produced by alternative splicing and their association with myasthenia gravis," Clinical Immunology (Sep. 2008) vol. 128, Issue 3, pp. 374-381.
Hursthouse et al., "Why Do Organic Compounds Crystallise Well or Badly or Ever so Slowly? Why Is Crystallisation Nevertheless Such a Good Purification Technique?," Organic Process Res & Devel (2009) vol. 13, No. 6, pp. 1231-1240.
Kakoulidou et al., "Human Soluble CD80 Is Generated by Alternative Splicing, and Recombinant Soluble CD80 Binds to CD28 and CD152 Influencing T-cell Activation," Scandinavian J. Immunol (Nov. 2007) 66(5):529-537.
Kanzaki et al., "Effective Production of Dehydro Cyclic Dipeptide Albonoursin Exhibiting Pronuclear Fusion Inhibitory Activity, I. Taxonomy and Fermentation," The Journal of Antibiotics, (1999) 52: 1017-1022.
Krendel et al., Apr. 2002, Nucelotide exchange factor GEF-H1 mediates cross-talk between microtubules and the actin cytoskeleton, Nature Cell Biology, 4:294-301 and supplementary information.
Lee et al., "A practical guide to pharmaceutical polymorph screening & selection," Asian Journal of Pharmaceutical Sciences (2014) vol. 9, pp. 163-175.
Li et al., May-Jun. 2017, Epitope mapping reveals the binding mechanism of a functional antibody cross-reactive to both human and murine programmed death 1, MABS, 9(4):628-637.
Liou et al., Aug. 12, 2004, Concise synthesis and structure-activity relationships of combretastatin A-4 analogues, 1-aroylindoles and 3-aroylindoles, as novel classes of potent antitubulin agents, Journal of Medicial Chemstry, 47(17):4247-4257.
Lu et al., Nov. 2012, An overview of tubulin inhibitors that interact with the colchicine binding site, Pharmaceutical Research, 29(11):2943-2971.
Melero et al., Aug. 2015, Evolving synergistic combinations of targeted immunotherapies to combat cancer, Nature Reviews Cancer, 15:457-472.
Mohanlal et al., Feb. 10, 2018, Plinabulin, a novel small molecule clinical stage I0 agent with anti-cancer activity, to prevent chemo-induced neutropenia and immune related AEs, Journal of Clinical Oncology, 36(5 Suppl):126.
Nabholz, 2001, Phase II study of docetaxel, doxorubiin, and cyclophosphamide as first-line chemotherapy for metastatic breast cancer, Journal of Clinical Oncology, 19:314-321.
Nielsen et al., Jun. 2005. Alternative splice variants of the human PD-1 gene, Cell Immunol., 235(2):109-116.
Ohaegbulam et al., "Human cancer immunotherapy with antibodies to the PD-1 and PD-L1 pathway," Trends Mol Med, (Oct. 30, 2014) 21(1): pp. 24-33.
Ott et al., "CTLA-4 and PD-1/PD-L1 Blockade: New Immunotherapeutic Modalities with Durable Clinical Benefit in Melanoma Patients," Clin Cancer Res (Oct. 1, 2013) 19(19): pp. 5300-5309.
Paik et al., "A Phase 2 Study of Weekly Albumin-Bound Paclitaxel (Abraxane®) Given as a Two-Hour Infusion", Cancer Chemother. Pharmacol., Nov. 2011, vol. 68, No. 5, pp. 1331-1337.
PRNewswire.com, Jun. 22, 2010, Nereus Pharmaceuticals completes enrollment of phase 2 advance clinical trial of plinabulin in non-small cell lung cancer, 4 pp.
Rathkopf, Jun. 20, 2008, Phase II trial of docetaxel with rapid androgen cycling for progressive noncastrate prostate cancer, J. Clin. Onc. 26(18):2959-2965.
Raza et al., 2014, Polymorphism: the phenomenon affecting the performance of drugs, SOJ Pharmacy & Pharmaceutical Sciences, 10 pp.
Remington, "The Science and Practice of Pharmacy, 20th Ed" (2000) p. 709.
Selby et al., Sep. 9, 2016, Preclinical development of ipilimumab and nivolumab combination immunotherapy: mouse tumor models, in vitro functional studies, and cynomolgus macaque toxicology, PloS One, 11(9):e0161779, 19 pp.
Sele et al., Jul. 2016, Novel 4-(pyrimidin-2-yl)morpholines targeting the colchicine-binding site of tubuline, Cancer Research, 76(14):abstract.
Spain et al., Feb. 6, 2016, Management of toxicities of immune checkpoint inhibitors, Cancer Treatment Reviews, 44:51-60.
Tonra et al., "Predictive models for tumour cell targeting with plinabulin, derived from in vitro screening and Affymetrix mRNA expression data," Proc Am Assoc Cancer Res (2019) vol. 60, p. 321, Abstract #1254.
Vainas, 2012, Personalising docetaxel and G-CSF schedules in cancer patients by a clinically validated computational model, British J. Cancer, 107:814-822.
Wailoo, 2009, The risk of febrile neutropenia in patients with non-small-cell lung cancer treated with docetaxel: a systematic review and meta-analysis, British J. Cancer 100(3):436-441.
Yamato et al., "Clinical importance of B7-H3 expression in human pancreatic cancer," British Journal of Cancer (Oct. 20, 2009) 101, pp. 1709-1716.
Buchbinder et al., Feb. 2016, CTLA-4 and PD-1 pathways: similarities, differences, and implications of their inhibition, American Journal of Clinical Oncology, 39(1):98-106.
Dalgleish, 2015, Rationale for combining immunotherapy with chemotherapy, Immunotherapy, 7(3):309-316.
Das et al., Feb. 1, 2015, Combination therapy with anti-CLTA4 and antiPD1 leads to distinct immunologic changes in-vivo, J. Immunolog, 194(3):950-959.
Fessas et al., 2017, A molecular and preclinical comparison of the PC-1-targeted t-cell checkpoint inhibitors nivolumab and mebrolizumag, Seminars in Oncology, 44:126-140.
Folkman, Dec. 2002, Role of angiogenesis in tumor growth and metastasis, Semin Oncol, 29:15-18.
Hellmann et al., Nov. 21, 2019, Nivolumab plus ipilimumab in advanced non-small-cell lung cancer, The New England Journal of Medicine, 381:2020-2031.
Hodi et al., Nov. 2016, Combined nivolumab and ipilimumab versus ipilimumab alone in patients with advanced melanoma: 2-year overall survival outcomes in a multicentre, randomised, controlled, phase 2 trial, Lancet Oncol., 17:1558-1568.
Intlekofer et al., Jul. 2013, At the bench: preclinical rationale for CTLA-4 and PD-1 blockade as cancer immunotherapy, J. Leukoc Biol., 94(1):25-39.
Kanojia et al., May 2015, βIII-tubulin regulates breast cancer metastases to the brain, Mol Cancer Ther., 14(5):1152-1161.
Kashyap et al., Sep. 24, 2019, GEF-H1 signaling upon microtubule destabilization is required for dendritic cell activation and specific anti-tumor responses, Cell Reports, 28:3367-3380.
Lloyd et al., 2015, Abstract A184: Activity of plinabulin in tumor models with kras mutations, Mol. Can. Thera. 14(12):Suppl. 2.

(56) References Cited

OTHER PUBLICATIONS

Natoli et al., Mar. 3, 2021. Plinabulin, a distinct microtubule-targeting chemotherapy, promotes M1-like macrophage polarization and anti-tumor immunity, Frontiers in Oncology, 11:1-14.

Riedel et al., Jun. 2007, A phase II trial of carboplatinvinorelbine with pegfilgrastim support for the treatment of patients with advanced non-small cell lung cancer, Journal of Thoracic Oncology, 2(6):520-525.

Snegovoy AV, et al. Practical recommendations for the appointment of colony-stimulating factors in order to prevent the development of febrile neuropathy in cancer patients // Practical recommendations. Version 2016. p. 394-401.

* cited by examiner

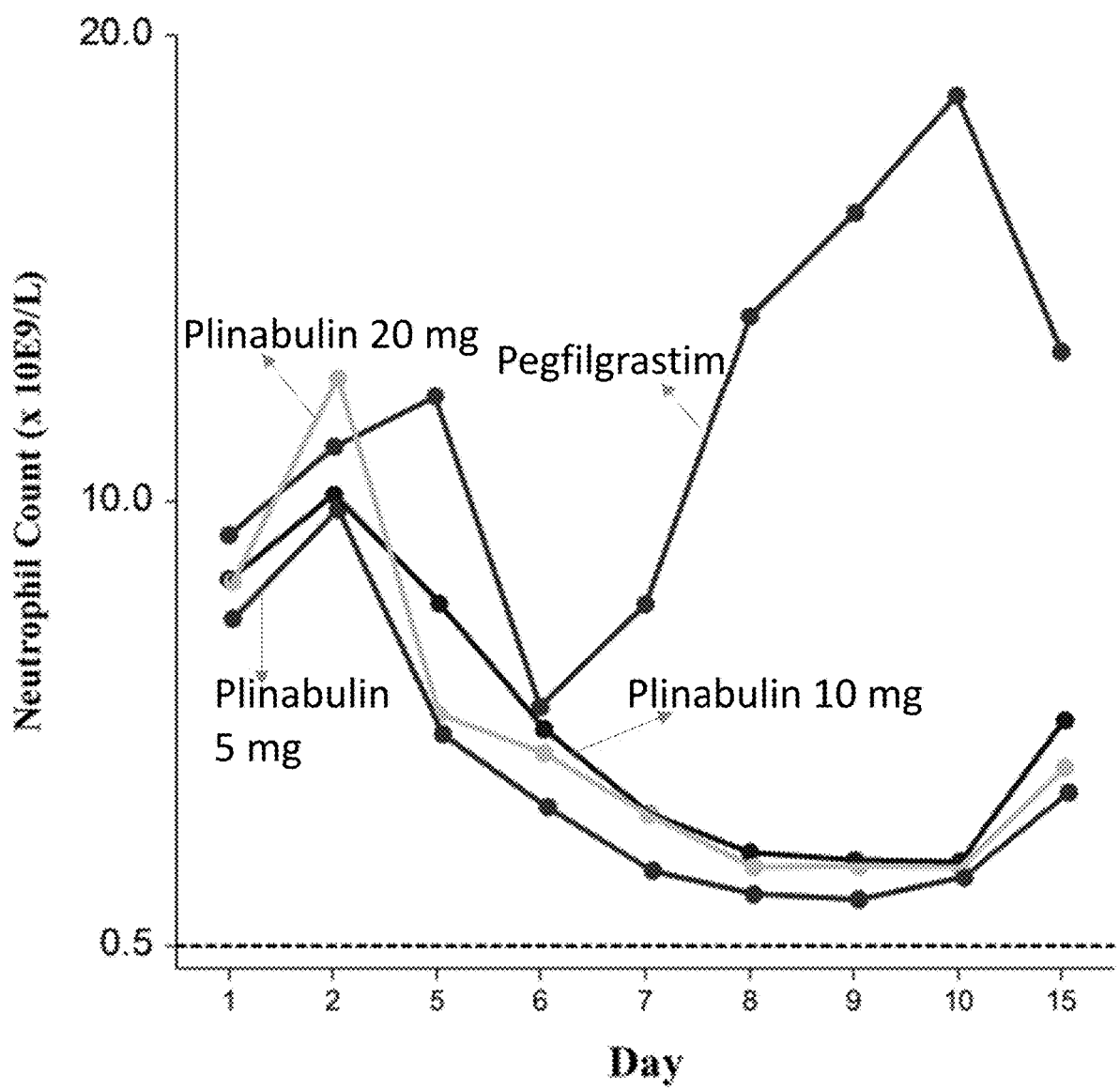

METHOD OF REDUCING CHEMOTHERAPY-INDUCED NEUTROPENIA

INCORPORATION BY REFERENCE TO ANY PRIORITY APPLICATIONS

This application is the U.S. National Phase of International Application No. PCT/US2018/016498 entitled METHOD OF REDUCING NEUTROPENIA, filed Feb. 1, 2018, which claims the benefit of U.S. Provisional Application No. 62/621,533, entitled Method of Reducing Neutropenia, filed Jan. 24, 2018, and U.S. Provisional Application No. 62/453,375, entitled Method of Reducing Neutropenia, filed Feb. 1, 2017, all of which are incorporated herein by reference in their entirety.

BACKGROUND

Field

The present invention relates to the field of chemistry and medicine. More particularly, the present invention relates to method of reducing or ameliorating neutropenia using Plinabulin.

Description of the Related Art

Myelosuppression is the primary toxicity of many chemotherapy regimens which often limits applicability. Both the duration of Grade 4 neutropenia and the depth of the neutrophil nadir have been correlated to severe and life-threatening infections. As a result, the prevention of neutropenia is a major goal for oncology practitioners for both safety and cost-efficiency and quality of life.

Neutropenia is a frequent and potentially life-threatening complication of cytotoxic myelosuppressive chemotherapy. Research has shown that patients who develop neutropenia are more susceptible to infections which often required treatment with antibiotics and in severe cases require hospitalization. Moreover, severe neutropenia often necessitates modification of the chemotherapy regimen, thereby compromising the ultimate success of the anticancer treatment plan.

SUMMARY

Some embodiments relate to a method of treating docetaxel-induced neutropenia in a subject, comprising administering a single dose of plinabulin in a 21-day docetaxel treatment cycle.

Some embodiments relate to a method of treating docetaxel-induced neutropenia in a subject, comprising administering plinabulin less than 2 hours after the administration of docetaxel.

Some embodiments relate to a method of treating docetaxel-induced neutropenia in a subject, comprising administering plinabulin at a dose less than 20 $mg/m^2$.

Some embodiments relate to a method of treating docetaxel-induced neutropenia in a subject, comprising administering a single dose of plinabulin in a 21-day docetaxel treatment cycle, wherein the amount of plinabulin administered is less than 30 $mg/m^2$ per treatment cycle.

Some embodiments relate to a method of treating Docetaxel, Doxorubicin, and Cyclophosphamide (TAC) or Docetaxel and Cyclophosphamide (TC) chemotherapy neutropenia in a subject, comprising administering a single dose of plinabulin in a 21-day TAC or TC chemotherapy treatment cycle.

Some embodiments relate to a method of treating a TAC or TC chemotherapy-induced neutropenia in a subject, comprising administering plinabulin less than 2 hours after the administration of TAC or TC chemotherapy.

Some embodiments relate to a method of treating a TAC or TC chemotherapy-induced neutropenia in a subject, comprising administering plinabulin at a dose less than 20 $mg/m^2$.

Some embodiments relate to a method of treating a TAC or TC chemotherapy-induced neutropenia in a subject, comprising administering a single dose of plinabulin in a 21-day TAC or TC chemotherapy treatment cycle, wherein the amount of plinabulin administered is less than 30 $mg/m^2$ per treatment cycle.

Some embodiments relate to a method of treating a chemotherapy induced neutropenia, comprising co-administering plinabulin and one or more G-CSF compound.

Some embodiments relate to a method of stimulating neutrophil survival, comprising co-administering plinabulin and one or more G-CSF compound.

Some embodiments relate to a method of treating a patient being administered with a docetaxel in an amount sufficient to cause neutropenia, the method comprising administering plinabulin at a dose effective to alleviate or prevent neutrophil reduction in the patient.

Some embodiments relate to a method of treating docetaxel induced neutropenia in a subject, comprising administering plinabulin at a dose in the range of about 1 $mg/m^2$ to about 50 $mg/m^2$.

Some embodiments relate to a treating docetaxel induced neutropenia in a subject having advanced for metastatic breast cancer, comprising: identifying a patient having advanced or metastatic breast cancer; and administering plinabulin at a dose in the range of about 1 $mg/m^2$ to about 50 $mg/m^2$.

Some embodiments relate to a method of treating docetaxel induced neutropenia in a subject having non-small cell lung cancer, comprising identifying a patient having non-small cell lung cancer; and administering plinabulin at a dose in the range of about 1 $mg/m^2$ to about 50 $mg/m^2$.

Some embodiments relate to a method of treating docetaxel induced neutropenia in a subject having hormone refractory metastatic prostate cancer, comprising: identifying a patient having hormone refractory metastatic prostate cancer; and administering plinabulin at a dose in the range of about 1 $mg/m^2$ to about 50 $mg/m^2$.

Some embodiments relate to a method of stimulating neutrophil survival, comprising administering plinabulin at a dose in the range of about 1 $mg/m^2$ to about 50 $mg/m^2$.

Some embodiments relate to a pharmaceutical composition comprising about 1 mg to about 150 mg, 1 mg to about 100 mg or about 1 mg to about 40 mg of plinabulin.

Some embodiments relate to a sterile container comprising a docetaxel, and about 1 mg to about 150 mg, 1 mg to about 100 mg or about 1 mg to about 40 mg of plinabulin, wherein the docetaxel and the plinabulin are provided in two separate sterile containers.

BRIEF DESCRIPTION OF THE DRAWINGS

FIG. 1 shows the change of neutrophil count through time with the treatment of plinabulin versus pegfilgrastim.

DETAILED DESCRIPTION OF THE PREFERRED EMBODIMENT

Plinabulin, (3Z,6Z)-3-Benzylidene-6-{[5-(2-methyl-2-propanyl)-1H-imidazol-4-yl]methylene}-2,5-piperazinedione, is a synthetic analog of the natural compound phenylahistin. Plinabulin can be readily prepared according to methods and procedures detailed in U.S. Pat. Nos. 7,064,201 and 7,919,497, which are incorporated herein by reference in their entireties. In some embodiments, Plinabulin can efficiently promote antigen uptake and migration of dendritic cells to lymph nodes where tumor-specific antigens are presented by dendritic cells to prime immune effector cells. Exposure of dendritic cells to Plinabulin can induce maturation of dendritic cells and significantly increase their capacity to prime T cells. In some embodiments, Plinabulin can mediate tumor size reduction through immune modulation of the tumor microenvironment to promote anti-tumor immune enhancing effects. In some embodiments, substantial therapeutic synergies can be achieved when combining Plinabulin with G-CSF.

Plinabulin is a small molecule with tumor-inhibiting and immune-enhancing effects. Plinabulin induces dendritic cell maturation and cytokines interleukin-1β (IL-1β), IL-6, and IL-12 production, all of which are important in neutrophil survival. Plinabulin also induces production of MHCII, CD40, CD80 and CD86 and related antigen-specific T-cell activation. Plinabulin may induce maturation of dendritic cells, resulting in the release of the cytokines interleukin (IL)-1β, IL-6 and IL-12 from monocytes/dendritic cells, and the cytokines protect neutrophils against apoptosis. In particular IL-6 can be mediated in the prevention of neutrophil apoptosis and IL-1β with increased neutrophil count. Plinabulin can prevent docetaxel- or cyclophosphamide-induced neutropenia via a mechanism of action different from that of G-CSF analogues. When used for treating solid tumor, plinabulin showed protective effect against neutropenia. In a Phase 2 (Ph2) trial, the addition of Plinabulin to Docetaxel (Plin+Doc; n=38) in NSCLC patients (pts) with a measurable lesion, improved mOS with 4.6 mo vs Doc alone (n=38). DOR (a marker of immune effect) was ~1 yr longer (P<0.05) with Plinabulin+Docetaxel vs Docetaxel alone. Plin exerted immune-enhancing effects (DOR), without increasing Immune-Related AEs (IR-AEs).

Granulocyte-colony stimulating factor (G-CSF) refers to compounds or factors that stimulate proliferation, differentiation, commitment and end cell functional activation of granulocytes in an animal, including a human subject. The term G-CSF or G-CSF variant includes all naturally occurring variants of G-CSF (with or without a leader sequence), G-CSF biosimilars, as well as G-CSF proteins derived therefrom which are modified by recombinant DNA technology, in particular fusion proteins which contain further polypeptide sequences apart from the G-CSF moiety. For example, one may: (1) increase half-life (or prepare an oral dosage form, for example) of the G-CSF molecule by, for example, decreasing the ability of proteases to act on the G-CSF molecule or adding chemical modifications to the G-CSF molecule, such as one or more polyethylene glycol molecules or enteric coatings for oral formulation which would act to change some characteristic of the G-CSF molecule as described above, such as increasing serum or other half-life or decreasing antigenicity; (2) prepare a hybrid molecule, such as combining G-CSF with part or all of another protein such as another cytokine or another protein which effects signal transduction via entry through the cell through a G-CSF-G-CSF receptor transport mechanism; or (3) increase the biological activity as in, for example, the ability to selectively stimulate neutrophils (as compared to a non-modified G-CSF molecule). G-CSF includes derivatives, mimetics, variants and chemically modified compounds or hybrids thereof as described in U.S. Pat. Nos. 5,399,345; 5,416,195; 5,981,551; 6,166,183 and 6,261,550, the contents of which are incorporated by reference in entireties. G-CSF compounds include but are not limited to filgrastim and pegfilgrastim. Examples of G-CSF that are commercially available include but are not limited to Neupogen® (Amgen), Tevagrastim® (Teva), Biograstim® (CT Arzneimittel), Ratiograstim® (Ratiopharm GmbH)), Zarxio® (Sandoz GmbH), Filgrastim Hexal® (Hexal AG), Neulasta® (Amgen), Granocyte® and Neutrogin® (Chugai), and Neu-up® (Kyowa Hakko). G-CSF is often given to manage chemotherapy-induced severe neutropenia. G-CSF such as pegfilgrastim is a colony-stimulating factor that acts on hematopoietic cells by binding to specific cell surface receptors, thereby stimulating proliferation, differentiation, commitment, and end cell functional activation.

Febrile neutropenia (FN) is a potentially life-threatening condition characterized by the development of fever (≥38.3° C.) and docetaxel-induced neutropenia (absolute neutrophil count [ANC]<$0.5 \times 10^9$/L). The risk of severe neutropenia including FN is mitigated by reducing docetaxel dosages or extending the dosing interval of the agents. However, research has shown these measures are directly correlated to lower long-term survival rates because of the relative reduction in the dose intensity of the drug. Therefore, granulocyte colony-stimulating factor (G-CSF) such as filgrastim (Neupogen®) or pegfilgrastim (Neulasta®), can be given to manage chemotherapy-induced severe neutropenia and to allow chemotherapy to be administered more effectively. According to these guidelines, prophylactic G-CSF use is recommended for patients at significant risk of FN based on the chemotherapy regimen and patient specific risk factors. However, the prophylactic use of G-CSF has some significant limitations in terms of safety, cost and convenience of use. Treatment should be administered within 14 days of chemotherapy initiation. Moreover, G-CSF therapy cannot be initiated until 24 hours after the last dose of chemotherapy for each treatment cycle and is generally administered once per chemotherapy cycle (requires baseline complete blood count [CBC] and platelet count during therapy). The concern with administering G-CSF on the day of chemotherapy is that increasing growth of myeloid cells may increase sensitivity to cytotoxic chemotherapy agents. Since cytotoxic chemotherapy causes the most damage to rapidly growing cells, giving an agent that causes myeloid cells to grow faster while chemotherapy is present may cause more toxicity. Duration of G-CSF therapy is to attenuate chemotherapy-induced neutropenia and is dependent on the myelosuppressive potential of chemotherapy regimen employed. Patients are required to either self-administer the drug or return to the center for treatment and evaluation which is often difficult and costly for the patient.

Warnings and precautions for pegfilgrastim include splenic rupture, acute respiratory distress syndrome, allergic reactions including anaphylaxis, fatal sickle cell crisis, glomerulonephritis, capillary leak syndrome, and leukocytosis. The most common adverse reactions are bone pain and pain in an extremity which occurred in 31% and 9% of patients, respectively. Additional notable adverse events include acute febrile neutrophilic dermatosis, cutaneous vaculitis and injection site reactions.

Plinabulin can be effective in ameliorating docetaxel-related severe neutropenia (including FN) and has a better safety profile (much less bone pain) and is more convenient for the patient by reducing the number of required patient visits and potentially also reducing the burden to the healthcare system. Most importantly, plinabulin can be given after a docetaxel cycle (e.g., 30 mins or 1 hour) as opposed to 24 hours after the completion of the cycle (as prescribed by pegfilgrastim, G-CSF and its biosimilars).

Patients with solid tumors who have received plinabulin monotherapy treatment (in the absence of chemotherapy), did not experience any clinically significant deleterious changes in hematology or chemistry laboratory parameters; however, there was a significantly lower incidence of neutropenia in patients receiving plinabulin plus docetaxel compared with the docetaxel monotherapy arm.

Clinical complications of neutropenia (febrile neutropenia, infections, sepsis, and mortality) occur with Grade 4 Neutropenia, as compared to with Grade 2 or 3 Neutropenia. For regulatory approval, the FDA and Health Authorities focus on Grade 4 Neutropenia data. Grade 4 Neutropenia/Severe Neutropenia is an Absolute Neutrophil Count of $<0.5 \times 10^9/L$. In animal model studies, Plinabulin has been shown to prevent neutropenia caused by number of chemotherapies with different mechanisms: docetaxel, cisplatin, adriamycin, cyclosphosphamide, topotecan, and gemcitabine. Table 1 shows many advantages plinabulin has over G-CSF drug for treating or attenuating neutropenia.

TABLE 1

Plinabulin has a superior product profile vs. G-CSF/neulasta

|  | G-CSF | Plinabulin |
| --- | --- | --- |
| Therapy Type | Growth factor | Anti-cancer agent |
| Bone Pain (% of patients) | >20%[1] | <4% |
| Hospitalization (% of patients) | 20% | 6% |
| Dose Administration | 24 hours after chemotherapy | 0.5-1 hour after chemotherapy |
| Therapy Type | Biologic | Small molecule |

Compared to docetaxel treatment alone, the addition of plinabulin to docetaxel significantly (p<0.0003) reduced the proportion of patients with Grade 4 neutropenia from 33.3% to 4.6% in Cycle 1. Data shows decrease in the proportions of patients with Grade 4 neutropenia (absolute neutrophil count [ANC]<$0.5 \times 10^9/L$) on Day 8, the approximate day after docetaxel administration corresponding to the largest reduction in neutrophil count. Plinabulin also reduced the clinical sequelae associated with docetaxel-induced neutropenia (sepsis, infections, hospitalizations, need for docetaxel dose reductions, and G-CSF use). Bone pain was reported in 4% of patients receiving plinabulin. Plinabulin has a favorable safety profile; the most prominent finding was Grade 3 transient hypertension in 20% and 5% of patients receiving 30 mg/m$^2$ and 20 mg/m$^2$ plinabulin, respectively.

Plinabulin can be effective for the mitigation of docetaxel-induced neutropenia. Administered by IV infusion on the same day of (approximately 30 mins or 1 hour after) docetaxel administration, plinabulin can be given in a single dose to be determined per cycle. Plinabulin has the potential to be an effective, safe (with much less bone pain), cost-effective, and convenient alternative to G-CSF for the prevention of docetaxel-induced neutropenia.

In some embodiments, the combination of plinabulin and G-CSF (e.g. pegfilgrastim or filgrastim) can work synergistically to treat or prevent neutropenia occurred during the chemotherapy or radiation therapy. The combination of plinabulin and G-CSF (e.g. pegfilgrastim or filgrastim) can help manage chemotherapy-induced severe neutropenia, maintain the patent's neutrophil count during treatment, and allow chemotherapy to be administered more effectively.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition.

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable salts can also be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as Li$^+$, Na$^+$, K$^+$, Mg$^{2+}$ and Ca$^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

Method of Treatment

Plinabulin can be effective in ameliorating or treating chemotherapy related (e.g., docetaxel, TAC, or TC-related) severe neutropenia (including FN) and has a better safety profile. Patients receiving Plinabulin treatment showed less bone pain, lower hospitalization frequency, and lower frequency of grade 4 neutropenia in cycle 1 when compared with other treatment methods (e.g., G-CSF). In addition, Plinabulin treatment also resulted in minimum or less febrile neutropenia when compared with other treatment methods (e.g., G-CSF). The patient can have better quality of life due to the superior properties of Plinabulin.

In some embodiments, the chemotherapy includes only docetaxel and no other additional chemotherapeutic agent.

In some embodiments, plinabulin can be co-administered with G-CSF to reduce, ameliorate, or present neutropenia induced by a chemotherapy or radiation therapy. In some embodiments, plinabulin can be co-administered with G-CSF to stimulate neutrophil production or proliferation. In some embodiments, plinabulin can be co-administered with G-CSF to reduce, ameliorate, or prevent neutropenia caused by docetaxel. Consistent with the benefit of neutropenia prevention, patients receiving plinabulin may require less G-CSF treatment. The co-administration of plinabulin and G-CSF can work synergistically to continuously maintain the patient's neutrophil count and reduce the risk of terminating the chemotherapy due to severe adverse effect.

Some embodiments include co-administering a composition, and/or pharmaceutical composition described herein, with an additional medicament. For example, as described above, some embodiments include co-administering plinabulin and one or more G-CSF drug. By "co-administration," it is meant that the two or more agents are administered in such a manner that administration of one or more agent has a broad effect at the same time as the one or more other agent, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally or intravenously. In another embodiment, the agents are administered through different routes, such as one being administered orally and another being administered i.v. In some embodiments, the time period between administration of one or more agent and administration of the co-administered one or more agent can be about 5 min, 10 min, 20 min, 30 min, 40 min, 45 min, 50 min, 55 min, 1 hour, 65 min, 70 min, 75 min, 90 min, 2 hours, 3 hours, 5 hours, 8 hours, 10 hours, 12 hours, 15 hours, 18 hours, 20 hours, 24 hours, 36 hours, 48 hours, 3 days, 4 days, 5 days, 6 days, 7 days, 10 days, 14 days, 21 days, 28 days, or 30 days. In some embodiments, the time period between administration of one or more agent and administration of the co-administered one or more agent can be in the range of about 1 min-5 min, 1 min-10 min, 1 min-20 min, 1 min-30 min, 1 min-40 min, 1 min-50 min, 1 min-1 h, 1 min-2 h, 1 min-4 h, 1 min-6 h, 1 min-8 h, 1 min-10 h, 1 min-12 h, 1 min-24 h, 1 min-36 h, 1 min-48 h, 1 min-60 h, 1 min-72 h, 5 min-10 min, 5 min-20 min, 5 min-30 min, 5 min-40 min, 5 min-50 min, 5 min-1 h, 5 min-75 min, 5 min-2 h, 5 min-4 h, 5 min-6 h, 5 min-8 h, 5 min-10 h, 5 min-12 h, 5 min-24 h, 5 min-36 h, 5 min-48 h, 5 min-60 h, 5 min-72 h, 10 min-20 min, 10 min-30 min, 10 min-40 min, 10 min-50 min, 10 min-1 h, 10 min-75 min, 10 min-2 h, 10 min-4 h, 10 min-6 h, 10 min-8 h, 10 min-10 h, 10 min-12 h, 10 min-24 h, 10 min-36 h, 10 min-48 h, 10 min-60 h, 10 min-72 h, 30 min-40 min, 30 min-50 min, 30 min-1 h, 30 min-75 min, 30 min-2 h, 30 min-4 h, 30 min-6 h, 30 min-8 h, 30 min-10 h, 30 min-12 h, 30 min-24 h, 30 min-36 h, 30 min-48 h, 30 min-60 h, 30 min-72 h, 1 h-2 h, 1 h-4 h, 1 h-6 h, 1 h-8 h, 1 h-10 h, 1 h-12 h, 1 h-24 h, 1 h-36 h, 1 h-48 h, 1 h-60 h, 1 h-72 h, 6 h-8 h, 6 h-10 h, 6 h-12 h, 6 h-24 h, 6 h-36 h, 6 h-48 h, 6 h-60 h, 6 h-72 h, 12 h-24 h, 12 h-36 h, 12 h-48 h, 12 h-60 h, or 12 h-72 h.

Patients receiving plinabulin treatment are less likely to require chemotherapy (e.g., docetaxel, TAC, or TC) dose reduction. The safety profile of plinabulin is better than other drugs that are used to treat or ameliorate docetaxel induced neutropenia (e.g., G-CSF treatment).

Patients receiving plinabulin treatment can show at least one of the following conditions: 1) lower incidence of Grade 4 neutropenia (absolute neutrophil count [ANC]<0.5×109/L); 2) lower incidence of febrile neutropenia (FN) (ANC<0.5×109/L and body temperature ≥38.3° C.); 3) higher neutrophil count during the treatment cycle; 4) lower incidence of documented infections in Cycles 1 to 4; 5) lower incidence and shorter duration of hospitalizations, and lower mortality due to FN during the treatment cycle; 6) better health-related Quality of Life. When compared with the G-CSF treatment (e.g., pegfilgrastim or filgrastim), plinabulin treatment showed lower incidence of antibiotic use, lower incidence of docetaxel dose delay, dose reduction, and/or dose discontinuation, lower Incidence, occurrence, and severity of adverse events (AEs)/serious adverse events (SAEs), lower incidence, occurrence and severity of bone pain, better systemic tolerance (physical examination and safety laboratory assessments).

In some embodiments, the chemotherapy can independently include one or more agents selected from the group consisting of methotrexate, vinblastine, doxorubicin, cisplatin, MVAC (methotrexate, vinblastine, doxorubicin and cisplatin), docetaxel, trastuzumab, cyclophosphamide, paclitaxel, dose-dense AC followed by T (i.e., doxorubicin, cyclophosphamide, paclitaxel), TAC (docetaxel, doxorubicin, cyclophosphamide), fluorouracil, bleomycin, etoposide, vincristine, procarbazine, prednisone, BEACOPP (bleomycin, etoposide, doxorubicin, cyclophosphamide, vincristine, procarbazine, prednisone), gemcitabine, ifosfamide, carboplatin, ICE (ifosfamide, carboplatin, etoposide), rituximab, RICE (rituximab, ifosfamide, carboplatin, etoposide), CHOP-14 (cyclophosphamide, doxorubicin, vincristine, prednisone), mesna, novantrone, MINE (mesna, ifosfamide, novantrone, etoposide), dexamethasone, cytarabine DHAP (dexamethasone, cisplatin, cytarabine), methylprednisolone, ESHAP (etoposide, methylprednisolone, cisplatin, cytarabine), HyperCVAD and rituximab (cyclophosphamide, vincristine, doxorubicin, dexamethasone, rituximab), dacarbazine, vinblastine, dacarbazine-based combination (dacarbazine, cisplatin, vinblastine), dacarbazine-based combination with IL-2 and interferon alfa (dacarbazine, cisplatin, vinblastine, IL-2, interferon alfa), topotecan, MAID (mesna, doxorubicin, ifosfamine, dacarbazine), VeIP (vinblastine, ifosfamide, cisplatin), VIP (etoposide, ifosfamide, cisplatin), TIP (paclitaxel, ifosfamide, cisplatin), gemcitabine, CMF classic (cyclophosphamide, methotrexate, fluorouracil), AC (doxorubicin, cyclophosphamide), FEC (fluorouracil, epirubicin, cyclophosphamide), TC (docetaxel, cyclophosphamide), cisplatin/topotecan, paclitaxel/cisplatin, irincotecan, FOLFOX (fluorouracil, leucovorin, oxaliplatin), irincotecan/cisplatin, epirubicin/cisplatin/5-fluorouracil, epirubicin/cisplatin/capecitabine, DT-PACE (dexamethasone/thalidomide/cisplatin/doxorubicin/cyclophosphamide/etoposide), ET-PACE and bortezomib, EPOCH (etoposide, prednisone, vincristine, cyclophosphamide, doxorubicin), GDP (gemcitabine, dexamethasone, cisplatin), GDP and rituximab, FMR (fludarabine, mitoxantrone, rituximab, CHOP and rituximab (cyclophosphamide, doxorubicin, vincristine, prednisone, rituximab), cisplatin/paclitaxel, cisplatin/vinorelbine, cisplatin/docetaxel, ciaplatin/etoposide, carboplatin/paclitaxel, carboplatin/docetaxel, FOLFIRINOX (5-FU/leucovorin, irinotecan and oxaliplatin), cabazitaxel, etoposide/carboplatin, etoposide/cisplatin. In some embodiments, the chemotherapy can independently include one or more agents selected from the group consisting of methotrexate, vinblastine, doxorubicin, cisplatin, docetaxel, trastuzumab, cyclophosphamide, paclitaxel, fluorouracil, bleomycin, etoposide, vincristine, procarbazine, prednisone, gemcitabine, ifosfamide, carboplatin, mesna, novantrone, cytarabine methylprednisolone, rituximab dacarbazine, vinblastine, topotecan, gemcitabine, irincotecan, epirubicin, 5-fluorouracil, capecitabine, bortezomib, and cabazitaxel.

In some embodiments, the chemotherapy can include one or more agents selected from the group consisting of methotrexate, vinblastine, doxorubicin, cisplatin, MVAC (methotrexate, vinblastine, doxorubicin and cisplatin), trastuzumab, cyclophosphamide, dose-dense AC followed by T (i.e., doxorubicin, cyclophosphamide, paclitaxel), fluorouracil, bleomycin, etoposide, vincristine, procarbazine, prednisone, BEACOPP (bleomycin, etoposide, doxorubicin, cyclophosphamide, vincristine, procarbazine, prednisone), gemcitabine, ifosfamide, carboplatin, ICE (ifosfamide, carboplatin, etoposide), rituximab, RICE (rituximab, ifosfamide, carboplatin, etoposide), CHOP-14 (cyclophosphamide, doxorubicin, vincristine, prednisone), mesna, novantrone, MINE (mesna, ifosfamide, novantrone, etoposide), dexamethasone, cytarabine DHAP (dexamethasone, cisplatin, cytarabine), methylprednisolone, ESHAP (etoposide, methylprednisolone, cisplatin, cytarabine), HyperCVAD and rituximab (cyclophosphamide, vincristine, doxorubicin, dexamethasone, rituximab), dacarbazine, vinblastine, dacarbazine-based combination (dacarbazine, cisplatin, vinblastine), dacarbazine-based combination with IL-2 and interferon alfa (dacarbazine, cisplatin, vinblastine, IL-2, interferon alfa), topotecan, MAID (mesna, doxorubicin, ifosfamine, dacarbazine), VeIP (vinblastine, ifosfamide, cisplatin), VIP (etoposide, ifosfamide, cisplatin), TIP (paclitaxel, ifosfamide, cisplatin). In some embodiments, the gemcitabine, CMF classic (cyclophosphamide, methotrexate, fluorouracil), AC (doxorubicin, cyclophosphamide), FEC (fluorouracil, epirubicin, cyclophosphamide), cisplatin/topotecan, paclitaxel/cisplatin, irincotecan, FOLFOX (fluorouracil, leucovorin, oxaliplatin), irincotecan/cisplatin, epirubicin/cisplatin/5-fluorouracil, epirubicin/cisplatin/capecitabine, DT-PACE (dexamethasone/thalidomide/cisplatin/doxorubicin/cyclophosphamide/etoposide), ET-PACE and bortezomib, EPOCH (etoposide, prednisone, vincristine, cyclophosphamide, doxorubicin), GDP (gemcitabine, dexamethasone, cisplatin), GDP and rituximab, FMR (fludarabine, mitoxantrone, rituximab, CHOP and rituximab (cyclophosphamide, doxorubicin, vincristine, prednisone, rituximab), cisplatin/paclitaxel, cisplatin/vinorelbine, ciaplatin/etoposide, carboplatin/paclitaxel, FOLFIRINOX (5-FU/leucovorin, irinotecan and oxaliplatin), cabazitaxel, etoposide/carboplatin, etoposide/cisplatin. In some embodiments, the chemotherapy can include one or more agents selected from the group consisting of methotrexate, vinblastine, doxorubicin, cisplatin, trastuzumab, cyclophosphamide, fluorouracil, bleomycin, etoposide, vincristine, procarbazine, prednisone, gemcitabine, ifosfamide, carboplatin, mesna, novantrone, cytarabine methylprednisolone, rituximab dacarbazine, vinblastine, topotecan, gemcitabine, irincotecan, epirubicin, 5-fluorouracil, capecitabine, and bortezomib.

Some embodiments relate to a method of reducing or preventing neutropenia induced by chemotherapy, the method comprising administering plinabulin to the patient undergoing chemotherapy treatment. Some embodiments relate to a method of reducing or preventing neutropenia induced by docetaxel, the method comprising administering plinabulin to the patient undergoing docetaxel treatment.

Chemotherapy such as Taxotere, Adriamycin and Cyclophosphamide (TAC), and Taxotere and Cyclophosphamide (TC) can also cause severe neutropenia. TAC has a high risk ($>20\%$) of causing FN. In some embodiments, during the TAC chemotherapy, the doxorubicin component is omitted and the TA chemotherapy is administered. For example, during the TAC treatment, in cycles 2 to 4, the doxorubicin component may be omitted at the discretion of the investigator, i.e., TC may be administered instead of TAC. Some embodiments relate to a method of reducing or preventing neutropenia induced by TAC or TC, the method comprising administering plinabulin to the patient undergoing docetaxel treatment. In some embodiments, the chemotherapy includes only TAC and no other additional chemotherapeutic agent. In some embodiments, the chemotherapy includes only TC and no other additional chemotherapeutic agent. In some embodiments, the administration schedule of TAC includes Day 1: Doxorubicin 50 mg/m2 IV, followed by cyclophosphamide 500 mg/m2 IV, followed by docetaxel 75 mg/m2 IV after a 1-hr interval. In some embodiments, the administration schedule of TC includes: Day 1: Docetaxel 75 mg/m2 IV followed by cyclophosphamide 600 mg/m2 IV.

Plinabulin is useful in preventing, treating, or ameliorating neutrophil reduction arising from chemotherapy (e.g., docetaxel, TAC, or TC) treatment.

Some embodiments relate to a method of treating a patient being administered with docetaxel in an amount sufficient to cause neutropenia, the method comprising: administering plinabulin at a dose effective to alleviate or prevent neutrophil reduction in the patient. Some embodiments relate to a method of treating a patient being administered with chemotherapy in an amount sufficient to cause neutropenia, the method comprising: administering plinabulin at a dose effective to alleviate or prevent neutrophil reduction in the patient.

Some embodiments relate to a method of treating a patient being administered with chemotherapy in an amount sufficient to cause neutropenia, the method comprising: co-administering plinabulin and G-CSF to alleviate or prevent neutrophil reduction in the patient.

Some embodiments relate to using plinabulin to relieve the degree of neutropenia and to shorten the severe duration of neutropenia. Some embodiments relate to co-administering plinabulin and G-CSF to relieve the degree of neutropenia and to shorten the severe duration of neutropenia.

In some embodiments, the patient has an advanced or metastatic breast cancer, early stage breast cancer, non-small cell lung cancer, refractory metastatic prostate cancer.

Some embodiments relate to treating a chemotherapy (e.g., docetaxel, TAC, or TC) induced neutropenia in a subject having advanced for metastatic breast cancer, comprising identifying a patient having advanced or metastatic breast cancer; and administering a pharmaceutically effective amount of plinabulin.

Some embodiments relate to a method of treating chemotherapy (e.g., docetaxel, TAC, or TC) induced neutropenia in a subject having non-small cell lung cancer, comprising: identifying a patient having non-small cell lung cancer; and administering a pharmaceutically effective amount of plinabulin.

Some embodiments relate to a method of treating chemotherapy (e.g., docetaxel, TAC, or TC) induced neutropenia in a subject having hormone refractory metastatic prostate cancer, comprising: identifying a patient having hormone refractory metastatic prostate cancer; and administering a pharmaceutically effective amount of plinabulin.

In some embodiments, the neutropenia is a febrile neutropenia. In some embodiments, the neutropenia is a drug-induced neutropenia. In some embodiments, the neutropenia is a taxane-induced neutropenia.

Some embodiments relate to a method of stimulating neutrophil survival, comprising administering plinabulin at a dose in the range of about 1 mg/m$^2$ to about 50 mg/m$^2$. Some embodiments relate to a method of stimulating neutrophil survival, comprising co-administering plinabulin and one or more G-CSF compound.

In some embodiments, when plinabulin is used in treating neutropenia, the patient has an absolute neutrophil count (ANC) of less than 500 neutrophils/mcl or an ANC of less than 1000 neutrophils/mcl and a predicted decline of less than or equal to 500 neutrophils/mcl over the following 48 hours. In some embodiments, plinabulin is used in treating neutropenia in a patient having ANC of less than 100 neutrophils/mcl. In some embodiments, plinabulin is used in treating neutropenia in a patient having ANC of less than 500 neutrophils/mcl. In some embodiments, plinabulin is used in treating neutropenia in a patient having ANC of less than 1000, 900, 800, 700, 600, 500, 400, 300, 200, 100 or 50 neutrophils/mcl. In some embodiments, plinabulin is used in treating neutropenia in a patient having ANC in the range of about 1000-100, 900-100, 800-100, 700-100, 600-100, 500-100, 400-100, 300-100, 200-100, 1000-200, 900-200, 800-200, 700-200, 600-200, 500-200, 400-200, 300-200, 1000-300, 900-300, 800-300, 700-300, 600-300, 500-300, 400-300, 1000-400, 900-400, 800-400, 700-400, 600-400, 500-400, 1000-500, 900-500, 800-500, 700-500, or 600-500 neutrophils/mcl.

In some embodiments, the plinabulin is administered at a dose in the range of about 1-50 mg/m$^2$ of the body surface area. In some embodiments, the plinabulin is administered at a dose of less than about 20 mg/m$^2$ of the body surface area. In some embodiments, the plinabulin is administered at a dose in the range of about 10-30 or about 15-25 mg/m$^2$ of the body surface area. In some embodiments, the plinabulin is administered at a dose in the range of about 1-2, 1-3, 1-4, 1-5, 1-6, 1-7, 1-8, 1-9, 1-10, 1-11, 1-12, 1-13, 1-13.75, 1-14, 1-15, 1-16, 1-17, 1-18, 1-19, 1-20, 1-22.5, 1-25, 1-27.5, 1-30, 1.5-2, 1.5-3, 1.5-4, 1.5-5, 1.5-6, 1.5-7, 1.5-8, 1.5-9, 1.5-10, 1.5-11, 1.5-12, 1.5-13, 1.5-13.75, 1.5-14, 1.5-15, 1.5-16, 1.5-17, 1.5-18, 1.5-19, 1.5-20, 1.5-22.5, 1.5-25, 1.5-27.5, 1.5-30, 2.5-2, 2.5-3, 2.5-4, 2.5-5, 2.5-6, 2.5-7, 2.5-8, 2.5-9, 2.5-10, 2.5-11, 2.5-12, 2.5-13, 2.5-13.75, 2.5-14, 2.5-15, 2.5-16, 2.5-17, 2.5-18, 2.5-19, 2.5-20, 2.5-22.5, 2.5-25, 2.5-27.5, 2.5-30, 2.5-7.5, 3-4, 3-5, 3-6, 3-7, 3-8, 3-9, 3-10, 3-11, 3-12, 3-13, 3-13.75, 3-14, 3-15, 3-16, 3-17, 3-18, 3-19, 3-20, 3-22.5, 3-25, 3-27.5, 3-30, 3.5-6.5, 3.5-13.75, 3.5-15, 2.5-17.5, 4-5, 4-6, 4-7, 4-8, 4-9, 4-10, 4-11, 4-12, 4-13, 4-13.75, 4-14, 4-15, 4-16, 4-17, 4-18, 4-19, 4-20, 4-22.5, 4-25, 4-27.5, 4-30, 5-6, 5-7, 5-8, 5-9, 5-10, 5-11, 5-12, 5-13, 5-13.75, 5-14, 5-15, 5-16, 5-17, 5-18, 5-19, 5-20, 5-22.5, 5-25, 5-27.5, 5-30, 6-7, 6-8, 6-9, 6-10, 6-11, 6-12, 6-13, 6-13.75, 6-14, 6-15, 6-16, 6-17, 6-18, 6-19, 6-20, 6-22.5, 6-25, 6-27.5, 6-30, 7-8, 7-9, 7-10, 7-11, 7-12, 7-13, 7-13.75, 7-14, 7-15, 7-16, 7-17, 7-18, 7-19, 7-20, 7-22.5, 7-25, 7-27.5, 7-30, 7.5-12.5, 7.5-13.5, 7.5-15, 8-9, 8-10, 8-11, 8-12, 8-13, 8-13.75, 8-14, 8-15, 8-16, 8-17, 8-18, 8-19, 8-20, 8-22.5, 8-25, 8-27.5, 8-30, 9-10, 9-11, 9-12, 9-13, 9-13.75, 9-14, 9-15, 9-16, 9-17, 9-18, 9-19, 9-20, 9-22.5, 9-25, 9-27.5, 9-30, 10-11, 10-12, 10-13, 10-13.75, 10-14, 10-15, 10-16, 10-17, 10-18, 10-19, 10-20, 10-22.5, 10-25, 10-27.5, 10-30, 11.5-15.5, 12.5-14.5, 7.5-22.5, 8.5-32.5, 9.5-15.5, 15.5-24.5, 5-35, 17.5-22.5, 22.5-32.5, 25-35, 25.5-24.5, 27.5-32.5, 2-20, t 2.5-22.5, or 9.5-21.5 mg/m$^2$, of the body surface area. In some embodiments, the plinabulin is administered at a dose of about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, the plinabulin is administered at a dose less than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, the plinabulin is administered at a dose greater than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40, 41, 42, 43, 44, 45, 46, 47, 48, 49, 50 mg/m$^2$ of the body surface area.

In some embodiments, when a single dose of plinabulin is administered once per chemotherapy (e.g., docetaxel, TAC, or TC) treatment cycle (e.g., 21 day), the total amount of plinabulin administered per treatment cycle of the chemotherapy is in the range of about 1-2, 1-3, 1-4, 1-5, 1-6, 1-7, 1-8, 1-9, 1-10, 1-11, 1-12, 1-13, 1-13.75, 1-14, 1-15, 1-16, 1-17, 1-18, 1-19, 1-20, 1-22.5, 1-25, 1-27.5, 1-30, 1.5-2, 1.5-3, 1.5-4, 1.5-5, 1.5-6, 1.5-7, 1.5-8, 1.5-9, 1.5-10, 1.5-11, 1.5-12, 1.5-13, 1.5-13.75, 1.5-14, 1.5-15, 1.5-16, 1.5-17, 1.5-18, 1.5-19, 1.5-20, 1.5-22.5, 1.5-25, 1.5-27.5, 1.5-30, 2.5-2, 2.5-3, 2.5-4, 2.5-5, 2.5-6, 2.5-7, 2.5-8, 2.5-9, 2.5-10, 2.5-11, 2.5-12, 2.5-13, 2.5-13.75, 2.5-14, 2.5-15, 2.5-16, 2.5-17, 2.5-18, 2.5-19, 2.5-20, 2.5-22.5, 2.5-25, 2.5-27.5, 2.5-30, 2.5-7.5, 3-4, 3-5, 3-6, 3-7, 3-8, 3-9, 3-10, 3-11, 3-12, 3-13, 3-13.75, 3-14, 3-15, 3-16, 3-17, 3-18, 3-19, 3-20, 3-22.5, 3-25, 3-27.5, 3-30, 3.5-6.5, 3.5-13.75, 3.5-15, 2.5-17.5, 4-5, 4-6, 4-7, 4-8, 4-9, 4-10, 4-11, 4-12, 4-13, 4-13.75, 4-14, 4-15, 4-16, 4-17, 4-18, 4-19, 4-20, 4-22.5, 4-25, 4-27.5, 4-30, 5-6, 5-7, 5-8, 5-9, 5-10, 5-11, 5-12, 5-13, 5-13.75, 5-14, 5-15, 5-16, 5-17, 5-18, 5-19, 5-20, 5-22.5, 5-25, 5-27.5, 5-30, 6-7, 6-8, 6-9, 6-10, 6-11, 6-12, 6-13, 6-13.75, 6-14, 6-15, 6-16, 6-17, 6-18, 6-19, 6-20, 6-22.5, 6-25, 6-27.5, 6-30, 7-8, 7-9, 7-10, 7-11, 7-12, 7-13, 7-13.75, 7-14, 7-15, 7-16, 7-17, 7-18, 7-19, 7-20, 7-22.5, 7-25, 7-27.5, 7-30, 7.5-12.5, 7.5-13.5, 7.5-15, 8-9, 8-10, 8-11, 8-12, 8-13, 8-13.75, 8-14, 8-15, 8-16, 8-17, 8-18, 8-19, 8-20, 8-22.5, 8-25, 8-27.5, 8-30, 9-10, 9-11, 9-12, 9-13, 9-13.75, 9-14, 9-15, 9-16, 9-17, 9-18, 9-19, 9-20, 9-22.5, 9-25, 9-27.5, 9-30, 10-11, 10-12, 10-13, 10-13.75, 10-14, 10-15, 10-16, 10-17, 10-18, 10-19, 10-20, 10-22.5, 10-25, 10-27.5, 10-30, 11.5-15.5, 12.5-14.5, 7.5-22.5, 8.5-32.5, 9.5-15.5, 15.5-24.5, 5-35, 17.5-22.5, 22.5-32.5, 25-35, 25.5-24.5, 27.5-32.5, 2-20, t 2.5-22.5, or 9.5-21.5 mg/m², of the body surface area. In some embodiments, the total amount of plinabulin administered per chemotherapy treatment cycle (e.g., 21 day) is about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m² of the body surface area. In some embodiments, the total amount of plinabulin administered per chemotherapy treatment cycle (e.g., 21 day) is less than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m² of the body surface area. In some embodiments, the total amount of plinabulin administered per chemotherapy treatment cycle (e.g., 21 day) is greater than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40, 41, 42, 43, 44, 45, 46, 47, 48, 49, 50 mg/m² of the body surface area. In some embodiments, the total amount of plinabulin administered per chemotherapy treatment cycle (e.g., 21 day) is about 20 mg/m² of the body surface area.

In some embodiments, the plinabulin dose is about 5 mg-300 mg, 5 mg-200 mg, 7.5 mg-200 mg, 10 mg-100 mg, 15 mg-100 mg, 20 mg-100 mg, 30 mg-100 mg, 40 mg-100 mg, 10 mg-80 mg, 15 mg-80 mg, 20 mg-80 mg, 30 mg-80 mg, 40 mg-80 mg, 10 mg-60 mg, 15 mg-60 mg, 20 mg-60 mg, 30 mg-60 mg, about 40 mg-60 mg, 1 mg-40 mg, 1 mg-35 mg, 1 mg-30 mg, 10 mg-40 mg, 10 mg-35 mg, or 20 mg-35 mg. In some embodiments, the plinabulin administered is about 20 mg-60 mg, 27 mg-60 mg, 20 mg-45 mg, or 27 mg-45 mg. In some embodiments, the plinabulin administered is about 5 mg-7.5 mg, 5 mg-9 mg, 5 mg-10 mg, 5 mg-12 mg, 5 mg-14 mg, 5 mg-15 mg, 5 mg-16 mg, 5 mg-18 mg, 5 mg-20 mg, 5 mg-22 mg, 5 mg-24 mg, 5 mg-26 mg, 5 mg-28 mg, 5 mg-30 mg, 5 mg-32 mg, 5 mg-34 mg, 5 mg-36 mg, 5 mg-38 mg, 5 mg-40 mg, 5 mg-42 mg, 5 mg-44 mg, 5 mg-46 mg, 5 mg-48 mg, 5 mg-50 mg, 5 mg-52 mg, 5 mg-54 mg, 5 mg-56 mg, 5 mg-58 mg, 5 mg-60 mg, 7 mg-7.7 mg, 7 mg-9 mg, 7 mg-10 mg, 7 mg-12 mg, 7 mg-14 mg, 7 mg-15 mg, 7 mg-16 mg, 7 mg-18 mg, 7 mg-20 mg, 7 mg-22 mg, 7 mg-24 mg, 7 mg-26 mg, 7 mg-28 mg, 7 mg-30 mg, 7 mg-32 mg, 7 mg-34 mg, 7 mg-36 mg, 7 mg-38 mg, 7 mg-40 mg, 7 mg-42 mg, 7 mg-44 mg, 7 mg-46 mg, 7 mg-48 mg, 7 mg-50 mg, 7 mg-52 mg, 7 mg-54 mg, 7 mg-56 mg, 7 mg-58 mg, 7 mg-60 mg, 9 mg-10 mg, 9 mg-12 mg, 9 mg-14 mg, 9 mg-15 mg, 9 mg-16 mg, 9 mg-18 mg, 9 mg-20 mg, 9 mg-22 mg, 9 mg-24 mg, 9 mg-26 mg, 9 mg-28 mg, 9 mg-30 mg, 9 mg-32 mg, 9 mg-34 mg, 9 mg-36 mg, 9 mg-38 mg, 9 mg-40 mg, 9 mg-42 mg, 9 mg-44 mg, 9 mg-46 mg, 9 mg-48 mg, 9 mg-50 mg, 9 mg-52 mg, 9 mg-54 mg, 9 mg-56 mg, 9 mg-58 mg, 9 mg-60 mg, 10 mg-12 mg, 10 mg-14 mg, 10 mg-15 mg, 10 mg-16 mg, 10 mg-18 mg, 10 mg-20 mg, 10 mg-22 mg, 10 mg-24 mg, 10 mg-26 mg, 10 mg-28 mg, 10 mg-30 mg, 10 mg-32 mg, 10 mg-34 mg, 10 mg-36 mg, 10 mg-38 mg, 10 mg-40 mg, 10 mg-42 mg, 10 mg-44 mg, 10 mg-46 mg, 10 mg-48 mg, 10 mg-50 mg, 10 mg-52 mg, 10 mg-54 mg, 10 mg-56 mg, 10 mg-58 mg, 10 mg-60 mg, 12 mg-14 mg, 12 mg-15 mg, 12 mg-16 mg, 12 mg-18 mg, 12 mg-20 mg, 12 mg-22 mg, 12 mg-24 mg, 12 mg-26 mg, 12 mg-28 mg, 12 mg-30 mg, 12 mg-32 mg, 12 mg-34 mg, 12 mg-36 mg, 12 mg-38 mg, 12 mg-40 mg, 12 mg-42 mg, 12 mg-44 mg, 12 mg-46 mg, 12 mg-48 mg, 12 mg-50 mg, 12 mg-52 mg, 12 mg-54 mg, 12 mg-56 mg, 12 mg-58 mg, 12 mg-60 mg, 15 mg-16 mg, 15 mg-18 mg, 15 mg-20 mg, 15 mg-22 mg, 15 mg-24 mg, 15 mg-26 mg, 15 mg-28 mg, 15 mg-30 mg, 15 mg-32 mg, 15 mg-34 mg, 15 mg-36 mg, 15 mg-38 mg, 15 mg-40 mg, 15 mg-42 mg, 15 mg-44 mg, 15 mg-46 mg, 15 mg-48 mg, 15 mg-50 mg, 15 mg-52 mg, 15 mg-54 mg, 15 mg-56 mg, 15 mg-58 mg, 15 mg-60 mg, 17 mg-18 mg, 17 mg-20 mg, 17 mg-22 mg, 17 mg-24 mg, 17 mg-26 mg, 17 mg-28 mg, 17 mg-30 mg, 17 mg-32 mg, 17 mg-34 mg, 17 mg-36 mg, 17 mg-38 mg, 17 mg-40 mg, 17 mg-42 mg, 17 mg-44 mg, 17 mg-46 mg, 17 mg-48 mg, 17 mg-50 mg, 17 mg-52 mg, 17 mg-54 mg, 17 mg-56 mg, 17 mg-58 mg, 17 mg-60 mg, 20 mg-22 mg, 20 mg-24 mg, 20 mg-26 mg, 20 mg-28 mg, 20 mg-30 mg, 20 mg-32 mg, 20 mg-34 mg, 20 mg-36 mg, 20 mg-38 mg, 20 mg-40 mg, 20 mg-42 mg, 20 mg-44 mg, 20 mg-46 mg, 20 mg-48 mg, 20 mg-50 mg, 20 mg-52 mg, 20 mg-54 mg, 20 mg-56 mg, 20 mg-58 mg, 20 mg-60 mg, 22 mg-24 mg, 22 mg-26 mg, 22 mg-28 mg, 22 mg-30 mg, 22 mg-32 mg, 22 mg-34 mg, 22 mg-36 mg, 22 mg-38 mg, 22 mg-40 mg, 22 mg-42 mg, 22 mg-44 mg, 22 mg-46 mg, 22 mg-48 mg, 22 mg-50 mg, 22 mg-52 mg, 22 mg-54 mg, 22 mg-56 mg, 22 mg-58 mg, 22 mg-60 mg, 25 mg-26 mg, 25 mg-28 mg, 25 mg-30 mg, 25 mg-32 mg, 25 mg-34 mg, 25 mg-36 mg, 25 mg-38 mg, 25 mg-40 mg, 25 mg-42 mg, 25 mg-44 mg, 25 mg-46 mg, 25 mg-48 mg, 25 mg-50 mg, 25 mg-52 mg, 25 mg-54 mg, 25 mg-56 mg, 25 mg-58 mg, 25 mg-60 mg, 27 mg-28 mg, 27 mg-30 mg, 27 mg-32 mg, 27 mg-34 mg, 27 mg-36 mg, 27 mg-38 mg, 27 mg-40 mg, 27 mg-42 mg, 27 mg-44 mg, 27 mg-46 mg, 27 mg-48 mg, 27 mg-50 mg, 27 mg-52 mg, 27 mg-54 mg, 27 mg-56 mg, 27 mg-58 mg, 27 mg-60 mg, 30 mg-32 mg, 30 mg-34 mg, 30 mg-36 mg, 30 mg-38 mg, 30 mg-40 mg, 30 mg-42 mg, 30 mg-44 mg, 30 mg-46 mg, 30 mg-48 mg, 30 mg-50 mg, 30 mg-52 mg, 30 mg-54 mg, 30 mg-56 mg, 30 mg-58 mg, 30 mg-60 mg, 33 mg-34 mg, 33 mg-36 mg, 33 mg-38 mg, 33 mg-40 mg, 33 mg-42 mg, 33 mg-44 mg, 33 mg-46 mg, 33 mg-48 mg, 33 mg-50 mg, 33 mg-52 mg, 33 mg-54 mg, 33 mg-56 mg, 33 mg-58 mg, 33 mg-60 mg, 36 mg-38 mg, 36 mg-40 mg, 36 mg-42 mg, 36 mg-44 mg, 36 mg-46 mg, 36 mg-48 mg, 36 mg-50 mg, 36 mg-52 mg, 36 mg-54 mg, 36 mg-56 mg, 36 mg-58 mg, 36 mg-60 mg, 40 mg-42 mg, 40 mg-44 mg, 40 mg-46 mg, 40 mg-48 mg, 40 mg-50 mg, 40 mg-52 mg, 40 mg-54 mg, 40 mg-56 mg, 40 mg-58 mg, 40 mg-60 mg, 43 mg-46 mg, 43 mg-48 mg, 43 mg-50 mg, 43 mg-52 mg, 43 mg-54 mg, 43 mg-56 mg, 43 mg-58 mg, 42 mg-60 mg, 45 mg-48 mg, 45 mg-50 mg, 45 mg-52 mg, 45 mg-54 mg, 45 mg-56 mg, 45 mg-58 mg, 45 mg-60 mg, 48 mg-50 mg, 48 mg-52 mg, 48 mg-54 mg, 48 mg-56 mg, 48 mg-58 mg, 48 mg-60 mg, 50 mg-52 mg, 50 mg-54 mg, 50 mg-56 mg, 50 mg-58 mg, 50 mg-60 mg, 52 mg-54 mg, 52 mg-56 mg, 52 mg-58 mg, or 52 mg-60 mg. In some embodiments, the plinabulin dose is greater than about 5 mg, about 10 mg, about 12.5 mg, about 13.5 mg, about 15 mg, about 17.5 mg, about 20 mg, about 22.5 mg, about 25 mg, about 27 mg, about 30 mg, about 35 mg, about 40 mg, about 50 mg, about 60 mg, about 70 mg, about 80 mg, about 90 mg, about 100 mg, about 125 mg, about 150 mg, or about 200 mg. In some embodiments, the plinabulin dose is about less than about 5 mg, about 10 mg, about 12.5 mg, about 13.5 mg, about 15 mg, about 17.5 mg, about 20 mg, about 22.5 mg, about 25 mg, about 27 mg, about 30 mg, about 35 mg, about 40 mg, about 50 mg, about 60 mg, about 70 mg, about 80 mg, about 90 mg, about 100 mg, about 125 mg, about 150 mg, or about 200 mg.

In some embodiments, the neutropenia is induced by a chemotherapy. The administration period can be a multi-week treatment cycle as long as the tumor remains under control and the regimen is clinically tolerated. In some embodiments, the chemotherapy and plinabulin can be administered once every three weeks. In some embodiments, the chemotherapy and plinabulin can be administered once every week, once every two weeks, once every three weeks, once every four weeks, once evert five weeks, or once every six weeks. In some embodiments, the chemotherapy and Plinabulin can be administered once a week, and preferably once on each of day 1 and day 8 of a three-week (21 day) treatment cycle. In some embodiments, the chemotherapy and Plinabulin can be administered once a week, twice a week, three times per week, four times per week, five times per week, six times per week, or daily during a one-week, two-week, three-week, four-week, or five-week treatment cycle. The administration can be on the same or different day of each week in the treatment cycle. In some embodiments, the plinabulin is administered prior to the chemotherapy administration. In some embodiments, the plinabulin is administered concurrently with the chemotherapy administration. In some embodiments, the plinabulin is administered after the chemotherapy administration.

In some embodiments, during the chemotherapy treatment cycle, the chemotherapeutic agent(s) is only administered once at the beginning of the treatment cycle, followed by the administration of plinabulin once, twice, three times, four times, five times, or six times during the treatment cycle. In some embodiments, during the chemotherapy treatment cycle, the chemotherapeutic agent(s) is only administered once at the beginning of the treatment cycle, followed by the administration of plinabulin once every week, once every two weeks, once every three weeks, once every four weeks, once evert five weeks, or once every six weeks. In some embodiments, during the chemotherapy treatment cycle, the chemotherapeutic agent(s) is only administered once at the beginning of the treatment cycle, followed by the administration of plinabulin once a week, twice a week, three times per week, four times per week, five times per week, six times per week, or daily during a one-week, two-week, three-week, four-week, or five-week treatment cycle.

In some embodiments, the neutropenia is induced by a docetaxel. The administration period can be a multi-week treatment cycle as long as the tumor remains under control and the regimen is clinically tolerated. In some embodiments, docetaxel and plinabulin can be administered once every three weeks. In some embodiments, docetaxel and plinabulin can be administered once every week, once every two weeks, once every three weeks, once every four weeks, once evert five weeks, or once every six weeks. In some embodiments, docetaxel and Plinabulin can be administered once a week, and preferably once on each of day 1 and day 8 of a three-week (21 day) treatment cycle. In some embodiments, docetaxel and Plinabulin can be administered once a week, twice a week, three times per week, four times per week, five times per week, six times per week, or daily during a one-week, two-week, three-week, four-week, or five-week treatment cycle. The administration can be on the same or different day of each week in the treatment cycle. In some embodiments, the plinabulin is administered prior to the docetaxel administration. In some embodiments, the plinabulin is administered concurrently with the docetaxel administration. In some embodiments, the plinabulin is administered after the docetaxel administration.

In some embodiments, the plinabulin is administered after the chemotherapy administration. When plinabulin is administered after the administration of a chemotherapy, it refers to administering plinabulin after the last chemotherapeutic agent(s) of the chemotherapy has been completely administered to the patients. For example, administering plinabulin about 30 mins after the administration of a TAC chemotherapy refers to begin the plinabulin administration about 30 mins after the administration of the last chemotherapeutic agent (e.g., docetaxel) has been completed. In some embodiments, the plinabulin is administered about 1 min, 5 min, 10 min, 15 min, 20 min, 25 min, 30 min, 45 min, 50 min, 1 h, 75 min, 1.5 h, 2 h, 2.5 h, 3 h, 4 h, 5 h, 6 h, 7 h, 8 h, 9 h, 10 h, 11 h, or 12 h after the administration of the chemotherapy. In some embodiments, the plinabulin is administered in less than about 1 min, 5 min, 10 min, 15 min, 20 min, 25 min, 30 min, 45 min, 50 min, 1 h, 75 min, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h after the administration of the chemotherapy. In some embodiments, the plinabulin is administered in more than about 1 min, 5 min, 10 min, 15 min, 20 min, 25 min, 30 min, 45 min, 50 min, 1 h, 75 min, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h after the administration of the chemotherapy. In some embodiments, the plinabulin is administered in about 1 min-5 min, 1 min-10 min, 1 min-15 min, 1 min-20 min, 1 min-25 min, 1 min-30 min, 1 min-45 min, 1 min-1 h, 1 min-75 min, 1 min-90 min, 1 min-120 min, 0.25 h-0.5 h, 0.25-0.75 h, 15 min-45 min, 15 min-75 min, 15 min-90 min, 15 min-120 min, 0.25-1 h, 30 min-45 min, 30 min-75 min, 30 min-90 min, 0.5 h-1 h, 0.5 h-2 h, 0.5 h-2.5 h, 1 h-2 h, 1 h-3 h, 1 h-5 h after the administration of the chemotherapy. In some embodiments, plinabulin is administered 30 mins after the chemotherapy administration. In some embodiments, plinabulin is administered in less than 1 hour after the chemotherapy administration.

In some embodiments, the plinabulin is administered after the docetaxel administration. In some embodiments, the plinabulin is administered about 1 min, 5 min, 10 min, 15 min, 20 min, 25 min, 30 min, 45 min, 50 min, 1 h, 75 min, 1.5 h, 2 h, 2.5 h, 3 h, 4 h, 5 h, 6 h, 7 h, 8 h, 9 h, 10 h, 11 h, or 12 h after the administration of docetaxel. In some embodiments, the plinabulin is administered in less than about 1 min, 5 min, 10 min, 15 min, 20 min, 25 min, 30 min, 45 min, 50 min, 1 h, 75 min, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h after the administration of docetaxel. In some embodiments, the plinabulin is administered in more than about 1 min, 5 min, 10 min, 15 min, 20 min, 25 min, 30 min, 45 min, 50 min, 1 h, 75 min, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h after the administration of docetaxel. In some embodiments, the plinabulin is administered in about 1 min-5 min, 1 min-10 min, 1 min-15 min, 1 min-20 min, 1 min-25 min, 1 min-30 min, 1 min-45 min, 1 min-1 h, 1 min-75 min, 1 min-90 min, 1 min-120 min, 0.25 h-0.5 h, 0.25-0.75 h, 15 min-45 min, 15 min-75 min, 15 min-90 min, 15 min-120 min, 0.25-1 h, 30 min-45 min, 30 min-75 min, 30 min-90 min, 0.5 h-1 h, 0.5 h-2 h, 0.5 h-2.5 h, 1 h-2 h, 1 h-3 h, 1 h-5 h after the administration of docetaxel. In some embodiments, plinabulin is administered 30 mins after the docetaxel administration. In some embodiments, plinabulin is administered in less than 1 hour after the docetaxel administration.

In some embodiments, when plinabulin is administered prior to the chemotherapy administration, the plinabulin is administered about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5 h-1 h, 0.5 h-2 h, 0.5 h-2.5 h, 1 h-2 h, 1 h-3 h, 1 h-5 h before the administration of the chemotherapy. In some embodiments, the plinabulin is administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, or 12 h before the administration of the chemotherapy. In some embodiments, the plinabulin is administered in less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h before the administration of the chemotherapy. In some embodiments, the plinabulin is administered in more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h before the administration of the chemotherapy.

In some embodiments, when plinabulin is administered prior to docetaxel administration, the plinabulin is administered about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5 h-1 h, 0.5 h-2 h, 0.5 h-2.5 h, 1 h-2 h, 1 h-3 h, 1 h-5 h before the administration of docetaxel. In some embodiments, the plinabulin is administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, or 12 h before the administration of docetaxel. In some embodiments, the plinabulin is administered in less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h before the administration of docetaxel. In some embodiments, the plinabulin is administered in more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h before the administration of docetaxel.

In some embodiments, the infusion time for plinabulin is about 1 min, 5 min, 10 min, 15 min, 20 min, 25 min, 30 min, 45 min, 50 min, 1 h, 75 min, 1.5 h, 2 h, 2.5 h, 3 h, 4 h, 5 h, 6 h, 7 h, 8 h, 9 h, 10 h, 11 h, or 12 h. In some embodiments, the infusion time for plinabulin is less than about 1 min, 5 min, 10 min, 15 min, 20 min, 25 min, 30 min, 45 min, 50 min, 1 h, 75 min, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h after. In some embodiments, the infusion time for plinabulin is greater than about 1 min, 5 min, 10 min, 15 min, 20 min, 25 min, 30 min, 45 min, 50 min, 1 h, 75 min, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h. In some embodiments, the infusion time for plinabulin is about 1 min-5 min, 1 min-10 min, 1 min-15 min, 1 min-20 min, 1 min-25 min, 1 min-30 min, 1 min-45 min, 1 min-1 h, 1 min-75 min, 1 min-90 min, 1 min-120 min, 0.25 h-0.5 h, 0.25-0.75 h, 15 min-45 min, 15 min-75 min, 15 min-90 min, 15 min-120 min, 0.25-1 h, 30 min-45 min, 30 min-75 min, 30 min-90 min, 0.5 h-1 h, 0.5 h-2 h, 0.5 h-2.5 h, 1 h-2 h, 1 h-3 h, 1 h-5 h. In some embodiments, the infusion time for plinabulin is 30 mins for a single dose (e.g., 5, 10, 20, or less than 30 mg/m$^2$,). In some embodiments, the infusion time for plinabulin is about 1 hour (e.g., 20, 30, or greater than 30 mg/m$^2$).

In some embodiments, the treatment schedule includes administration of the chemotherapy followed by the administration of plinabulin once every 3 weeks. In some embodiments, the treatment schedule includes administration of the chemotherapy followed by the administration of plinabulin about 30 mins after the chemotherapy administration, and the plinabulin is administered once every 3 weeks in a treatment cycle. In some embodiments, the treatment schedule includes administration of the chemotherapy followed by the administration of plinabulin once every week, 2 weeks, 3 weeks, 4 weeks, 5 weeks, 6 weeks, 7 weeks, or 8 weeks. In some embodiments, the treatment schedule includes administration of the chemotherapy followed by the administration of plinabulin two times every 1 week, 2 weeks, 3 weeks, 4 weeks, 5 weeks, 6 weeks, 7 weeks, or 8 weeks. In some embodiments, the treatment schedule includes administration of the chemotherapy followed by the administration of plinabulin once every week in a treatment cycle of 1 week, 2 weeks, 3 weeks, 4 weeks, 5 weeks, 6 weeks, 7 weeks, or 8 weeks. In some embodiments, the treatment schedule includes administration of the chemotherapy followed by the administration of plinabulin twice every 1 week in a treatment cycle of 1 week, 2 weeks, 3 weeks, 4 weeks, 5 weeks, 6 weeks, 7 weeks, or 8 weeks. In some embodiments, the treatment schedule includes administration of the chemotherapy followed by the administration of plinabulin on day 1, day 8, and day 15 of a 21-day treatment cycle. In some embodiments, the treatment schedule includes administering plinabulin following every dose of the chemotherapy administration. In some embodiments, the treatment schedule includes administering plinabulin following the initial dose/cycle of the chemotherapy administration and then administering plinabulin following every two doses, three doses, four doses, five doses, or six doses of the chemotherapy administration. In some embodiments, the treatment schedule includes administering plinabulin following every other dose of the chemotherapy administration. In some embodiments, the plinabulin is administered after every two doses, every three doses, every four doses, every five doses, or every six doses of the chemotherapy administration.

In some embodiments, the first dose of plinabulin is administered as soon as suspected or confirmed neutropenia development.

In some embodiments, the treatment schedule includes administration of the chemotherapy (e.g., docetaxel, TAC, or TC) followed by the administration of plinabulin once every 3 weeks. In some embodiments, the treatment schedule includes administration of the chemotherapy (e.g., docetaxel, TAC, or TC) followed by the administration of plinabulin about 30 mins after the chemotherapy administration, and the plinabulin is administered once every 3 weeks in a treatment cycle. In some embodiments, the treatment schedule includes administration of the chemotherapy (e.g., docetaxel, TAC, or TC) followed by the administration of plinabulin once every 1 week, 2 weeks, 3 weeks, 4 weeks, 5 weeks, 6 weeks, 7 weeks, or 8 weeks. In some embodiments, the treatment schedule includes administration of the chemotherapy (e.g., docetaxel, TAC, or TC) followed by the administration of plinabulin two times every 1 week, 2 weeks, 3 weeks, 4 weeks, 5 weeks, 6 weeks, 7 weeks, or 8 weeks. In some embodiments, the treatment schedule includes administration of the chemotherapy (e.g., docetaxel, TAC, or TC) followed by the administration of plinabulin once every 1 week in a treatment cycle of 1 week, 2 weeks, 3 weeks, 4 weeks, 5 weeks, 6 weeks, 7 weeks, or 8 weeks. In some embodiments, the treatment schedule includes administration of the chemotherapy (e.g., docetaxel, TAC, or TC) followed by the administration of plinabulin twice every 1 week in a treatment cycle of 1 week, 2 weeks, 3 weeks, 4 weeks, 5 weeks, 6 weeks, 7 weeks, or 8 weeks. In some embodiments, the treatment schedule includes administration of the chemotherapy (e.g., docetaxel, TAC, or TC) followed by the administration of plinabulin on day 1, day 8, and day 15 of a 21-day treatment cycle. In some embodiments, the treatment schedule includes administering plinabulin following every dose of the chemotherapy (e.g., docetaxel, TAC, or TC) administration. In some embodiments, the treatment schedule includes administering plinabulin following the initial dose of the chemotherapy (e.g., docetaxel, TAC, or TC) administration and then administering plinabulin following every two doses, three doses, four doses, five doses, or six doses of the chemotherapy administration. In some embodiments, the treatment schedule includes administering plinabulin following every other dose of the chemotherapy (e.g., docetaxel, TAC, or TC) administration. In some embodiments, the plinabulin is administered after every two doses, every three doses, every four doses, every five doses, or every six doses of the chemotherapy (e.g., docetaxel, TAC, or TC) administration.

In some embodiments, the treatment schedule includes administration of the chemotherapy (e.g., docetaxel, TAC, or TC) followed by the co-administration of plinabulin and G-CSF once every 3 weeks. In some embodiments, the treatment schedule includes administration of the chemotherapy (e.g., docetaxel, TAC, or TC) followed by the co-administration of plinabulin and G-CSF, and the plinabulin is administered once every 3 weeks in a treatment cycle. In some embodiments, the treatment schedule includes administration of the chemotherapy (e.g., docetaxel, TAC, or TC) followed by the co-administration of plinabulin and G-CSF once every 1 week, 2 weeks, 3 weeks, 4 weeks, 5 weeks, 6 weeks, 7 weeks, or 8 weeks. In some embodiments, the treatment schedule includes administration of the chemotherapy (e.g., docetaxel, TAC, or TC) followed by the administration of co-administration of plinabulin and G-CSF two times every 1 week, 2 weeks, 3 weeks, 4 weeks, 5 weeks, 6 weeks, 7 weeks, or 8 weeks. In some embodiments, the treatment schedule includes administration of the chemotherapy (e.g., docetaxel, TAC, or TC) followed by the co-administration of plinabulin and G-CSF once every 1 week in a treatment cycle of 1 week, 2 weeks, 3 weeks, 4 weeks, 5 weeks, 6 weeks, 7 weeks, or 8 weeks. In some embodiments, the treatment schedule includes administration of the chemotherapy (e.g., docetaxel, TAC, or TC) followed by the co-administration of plinabulin and G-CSF twice every 1 week in a treatment cycle of 1 week, 2 weeks, 3 weeks, 4 weeks, 5 weeks, 6 weeks, 7 weeks, or 8 weeks. In some embodiments, the treatment schedule includes administration of the chemotherapy (e.g., docetaxel, TAC, or TC) followed by the co-administration of plinabulin and G-CSF on day 1, day 8, and day 15 of a 21-day treatment cycle. In some embodiments, the treatment schedule includes co-administering plinabulin and G-CSF following every dose of the chemotherapy (e.g., docetaxel, TAC, or TC) administration. In some embodiments, the treatment schedule includes co-administering plinabulin and G-CSF following the initial dose of the chemotherapy (e.g., docetaxel, TAC, or TC) administration and then administering plinabulin following every two doses, three doses, four doses, five doses, or six doses of the chemotherapy administration. In some embodiments, the treatment schedule includes co-administering plinabulin and G-CSF following every other dose of the chemotherapy (e.g., docetaxel, TAC, or TC) administration. In some embodiments, the plinabulin and G-CSF are administered after every two doses, every three doses, every four doses, every five doses, or every six doses of the chemotherapy (e.g., docetaxel, TAC, or TC) administration.

In some embodiments, the treatment schedule includes administering plinabulin following every cycle of the chemotherapy (e.g., docetaxel, TAC, or TC) administration. In some embodiments, the treatment schedule includes administering plinabulin following the initial cycle of the chemotherapy (e.g., docetaxel, TAC, or TC) administration and then administering plinabulin following every two cycles, three cycles, four cycles, five cycles, or six cycles of the chemotherapy administration. In some embodiments, the treatment schedule includes administering plinabulin following every other cycle of the chemotherapy (e.g., docetaxel, TAC, or TC) administration. In some embodiments, the plinabulin is administered after every two cycles, every three cycles, every four cycles, every five cycles, or every six cycles of the chemotherapy (e.g., docetaxel, TAC, or TC) administration.

The treatment cycle can be repeated as long as the regimen is clinically tolerated. In some embodiments, the treatment cycle for docetaxel and plinabulin is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle.

In some embodiments, the use of plinabulin can reduce the incidence of Grade 4 neutropenia by at least about 1%, 2%, 3%, 4%, 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, or 100%. In some embodiments, the use of plinabulin can reduce the incidence of Grade 4 neutropenia by at least about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, or 100%. In some embodiments, the use of plinabulin can reduce the incidence of Grade 4 neutropenia by less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, or 100%. In some embodiments, the use of plinabulin can reduce the incidence of Grade 4 neutropenia in the range of about 1%-5%, 1%-10%, 1%-15%, 1%-20%, 1%-30%, 1%-40%, 1%-50%, 2.5%-10%, 2.5%-15%, 2.5%-20%, 2.5%-30%, 5%-10%, 5%-15%, 5%-20%, 5%-30%, 5%-40%, 10%-40%, 12.5%-40%, 5%-50%, 10%-50%, 12.5%-50%, 15%-50%, 17.5%-50%, 20%-50%, 25%-50%, 27.5%-50%, 30%-50%, 5%-60%, 10%-60%, 12.5%-60%, 15%-60%, 17.5%-60%, 20%-60%, 25%-60%, 27.5%-60%, 30%-60%, 35%-60%, 37.5%-60%, 40%-60%, 45%-70%, or 50%-80%.

In some embodiments, the use of plinabulin can be about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 4 neutropenia. In some embodiments, the use of plinabulin can be greater than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 4 neutropenia. In some embodiments, the use of plinabulin can be less than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 4 neutropenia. In some embodiments, the use of plinabulin can be greater than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 4 neutropenia.

In some embodiments, the co-administration of plinabulin and G-CSF can be about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 4 neutropenia. In some embodiments, the co-administration of plinabulin and G-CSF can be greater than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 4 neutropenia. In some embodiments, the co-administration of plinabulin and G-CSF can be less than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 4 neutropenia. In some embodiments, the co-administration of plinabulin and G-CSF can be greater than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 4 neutropenia.

In some embodiments, the use of plinabulin can reduce the duration of severe neutropenia by about 1%, 2%, 3%, 4%, 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the use of plinabulin can reduce the duration of severe neutropenia by greater than about 1%, 2%, 3%, 4%, 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the use of plinabulin can reduce the duration of severe neutropenia by less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the use of plinabulin can reduce the duration of severe neutropenia in the range of about 5%-10%, 5%-20%, 5%-30%, 5%-40%, 5%-50%, 5%-60%, 5%-70%, 5%-80%, 5%-100%, 5%-2 times, 5%-5 times, 5%-15 times, 20%-10 times, or 50%-500%.

In some embodiments, the co-administration of plinabulin and G-CSF can reduce the duration of severe neutropenia by about 1%, 2%, 3%, 4%, 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the co-administration of plinabulin and G-CSF can reduce the duration of severe neutropenia by greater than about 1%, 2%, 3%, 4%, 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the co-administration of plinabulin and G-CSF can reduce the duration of severe neutropenia by less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the co-administration of plinabulin and G-CSF can reduce the duration of severe neutropenia in the range of about 5%-10%, 5%-20%, 5%-30%, 5%-40%, 5%-50%, 5%-60%, 5%-70%, 5%-80%, 5%-100%, 5%-2 times, 5%-5 times, 5%-15 times, 20%-10 times, or 50%-500%.

In some embodiments, plinabulin can be about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim) in reducing the duration of severe neutropenia. In some embodiments, plinabulin can be greater than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim) in reducing the duration of severe neutropenia. In some embodiments, plinabulin can be less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim) in reducing the duration of severe neutropenia. In some embodiments, plinabulin can be in the range of about 5%-15 times, 20%-10 times, or 50%-500% more effective than G-CSF (e.g., pegfilgrastim) in reducing the duration of severe neutropenia.

In some embodiments, the co-administration of plinabulin and G-CSF can be about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim) in reducing the duration of severe neutropenia. In some embodiments, the co-administration of plinabulin and G-CSF can be greater than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim) in reducing the duration of severe neutropenia. In some embodiments, the co-administration of plinabulin and G-CSF can be less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim) in reducing the duration of severe neutropenia. In some embodiments, the co-administration of plinabulin and G-CSF can be in the range of about 5%-15 times, 20%-10 times, or 50%-500% more effective than G-CSF (e.g., pegfilgrastim) in reducing the duration of severe neutropenia.

For some embodiments, G-CSF can be administered with plinabulin in treating chemotherapy induced neutropenia as described above.

Plinabulin and G-CSF can be co-administered following the chemotherapy to treat or ameliorate neutropenia. In some embodiments, a single dose of G-CSF (e.g., pegfilgrastim or filgrastim) can be in the range of 0.5 mg to about 10 mg, from about 0.5 mg to about 8 mg, from about 0.5 mg to about 7 mg, from about 0.5 mg to about 6 mg, from about 0.5 mg to about 5 mg, from about 0.5 mg to about 4 mg, from about 0.5 mg to about 3 mg, 1 mg to about 100 mg, from about 1 mg to about 50 mg, from about 1 mg to about 25 mg, from about 1 mg to about 15 mg, from about 1 mg to about 10 mg, from about 1 mg to about 8 mg, from about 1 mg to about 7 mg, from about 1 mg to about 6 mg, from about 1 mg to about 5 mg, from about 1 mg to about 4 mg, from about 1 mg to about 3 mg, from about 2 mg to about 50 mg, from about 2 mg to about 25 mg, from about 2 mg to about 15 mg, from about 2 mg to about 10 mg, from about 2 mg to about 10 mg, from about 2 mg to about 8 mg, from about 2 mg to about 7 mg, from about 2 mg to about 6 mg, from about 2 mg to about 5 mg, from about 2 mg to about 4 mg, from about 2 mg to about 3 mg, from about 3 mg to about 50 mg, from about 3 mg to about 25 mg, from about 3 mg to about 15 mg, from about 3 mg to about 10 mg, from about 3 mg to about 10 mg, from about 3 mg to about 8 mg, from about 3 mg to about 7 mg, from about 3 mg to about 6 mg, from about 3 mg to about 5 mg, from about 3 mg to about 4 mg, from about 4 mg to about 50 mg, from about 4 mg to about 25 mg, from about 4 mg to about 15 mg, from about 4 mg to about 10 mg, from about 4 mg to about 6 mg, from about 4 mg to about 5 mg, from about 5 mg to about 25 mg, from about 5 mg to about 15 mg, from about 5 mg to about 10 mg, or from about 5 mg to about 8 mg. In some embodiments, a single dose of G-CSF (e.g., pegfilgrastim or filgrastim) may be from about 3 mg to about 10 mg, or from about 4 mg to about 8 mg. In some embodiments, a single dose of G-CSF (e.g., pegfilgrastim or filgrastim) may be greater than about 0.1 mg, about 0.2 mg, about 0.3 mg, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 7 mg, about 8 mg, about 9 mg, or about 10 mg. In some embodiments, a single dose of G-CSF (e.g., pegfilgrastim or filgrastim) may be less than about 1 mg, about 1.5 mg, about 2 mg, about 2.5 mg, about 3 mg, about 3.5 mg, about 4 mg, about 4.5 mg, about 5 mg, about 5.5 mg, about 6 mg, about 7 mg, about 8 mg, about 9 mg, about 10 mg, about 12.5 mg, or about 15 mg. In some embodiments, a single dose of G-CSF (e.g., pegfilgrastim or filgrastim) may be about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 7 mg, about 8 mg, about 9 mg, or about 10 mg. In some embodiments, a single dose of G-CSF (e.g., pegfilgrastim or filgrastim) may be about 6 mg.

Co-administration of Plinabulin and G-CSF can help prevent or treat severe neutropenia induced by the chemotherapy treatment. In some embodiments, the G-CSF (e.g., pegfilgrastim or filgrastim) is administered once per chemotherapy cycle. In some embodiments, the G-CSF (e.g., pegfilgrastim or filgrastim) is not administered between 14 days before and 24 hours after the administration of cytotoxic chemotherapy. In some embodiments, two doses of G-CSF (e.g., pegfilgrastim or filgrastim) are administered one week apart. In some embodiments, the G-CSF (e.g., pegfilgrastim or filgrastim) is administered once, twice, three times, or four times a week. In some embodiments, the G-CSF (e.g., pegfilgrastim or filgrastim) is administered once a week, every two weeks, every three weeks, every four weeks, every five weeks, or ever six weeks. In some embodiments, the first dose of G-CSF (e.g., pegfilgrastim or filgrastim) is administered as soon as the suspected or confirmed exposure to myelosuppressive chemotherapy or myelosuppressive dose of radiation. In some embodiments, the G-CSF (e.g., pegfilgrastim or filgrastim) is administered subcutaneously.

In some embodiments, during the chemotherapy treatment cycle, the chemotherapeutic agent(s) is only administered once at the beginning of the treatment cycle, followed by the co-administration of plinabulin and G-CSF once, twice, three times, four times, five times, or six times during the treatment cycle. In some embodiments, during the chemotherapy treatment cycle, the chemotherapeutic agent(s) is only administered once at the beginning of the treatment cycle, followed by the co-administration of plinabulin and G-CSF once every week, once every two weeks, once every three weeks, once every four weeks, once evert five weeks, or once every six weeks. In some embodiments, during the chemotherapy treatment cycle, the chemotherapeutic agent(s) is only administered once at the beginning of the treatment cycle, followed by the co-administration of plinabulin and G-CSF once a week, twice a week, three times per week, four times per week, five times per week, six times per week, or daily during a one-week, two-week, three-week, four-week, or five-week treatment cycle.

In some embodiments, the G-CSF and plinabulin can be co-administered once every three weeks. In some embodiments, the G-CSF and plinabulin can be co-administered once every week, once every two weeks, once every three weeks, once every four weeks, once evert five weeks, or once every six weeks. In some embodiments, the G-CSF and plinabulin can be co-administered once a week. In some embodiments, G-CSF and plinabulin can be co-administered once a week, twice a week, three times per week, four times per week, five times per week, six times per week, or daily during a one-week, two-week, three-week, four-week, or five-week treatment cycle. The administration can be on the same or different day of each week in the treatment cycle. In some embodiments, the plinabulin is administered prior to the G-CSF administration. In some embodiments, the plinabulin is administered concurrently with the G-CSF administration. In some embodiments, the plinabulin is administered after the G-CSF administration.

In some embodiments, the G-CSF is administered prior to the plinabulin administration. In some embodiments, the G-CSF is administered concurrently with the plinabulin administration. In some embodiments, the G-CSF is administered after the plinabulin administration.

In some embodiments, the G-CSF is administered after about 6 h, 12 h, 18 h, 24 h, 36 g, 48 h, or 72 h after the administration of the chemotherapy. In some embodiments, the G-CSF is administered in less than about 12 h, 18 h, 24 h, 36 h, 48 h, 60 h, 72 h, 84 h, 96 h, 5 days, 6 days, or 7 days after the administration of the chemotherapy. In some embodiments, the G-CSF is administered in about 1 h-24 h, 12 h-36 h, 10 h-40 h, 1 day-2 days, 1 day-5 days, 1 day-1 week after the administration of the chemotherapy. In some embodiments, the G-CSF is administered about 24 h after the chemotherapy administration.

Administration of the pharmaceutical compositions described herein can be via any of the accepted modes of administration for agents that serve similar utilities including, but not limited to, orally, sublingually, buccally, subcutaneously, intravenously, intranasally, topically, transdermally, intradermally, intraperitoneally, intramuscularly, intrapulmonarily, vaginally, rectally, or intraocularly. Oral and parenteral administrations are customary in treating the indications that are the subject of the preferred embodiments Pharmaceutical Composition Some embodiments relate to a pharmaceutical composition including plinabulin. Some embodiments relate to a pharmaceutical composition comprising about 1 mg to about 100 mg of plinabulin.

In some embodiments, the compositions described herein can be administered or used in combination with docetaxel treatment.

Other embodiments include co-administering Plinabulin and docetaxel in separate compositions or the same composition. Thus, some embodiments include a first pharmaceutical compositions comprising: (a) a safe and therapeutically effective amount of docetaxel or pharmaceutically acceptable salts thereof and (b) a pharmaceutically acceptable carrier, diluent, excipient or combination thereof; and a second pharmaceutical composition comprising: (a) a safe and therapeutically effective amount of plinabulin and (b) a pharmaceutically acceptable carrier, diluent, excipient or combination thereof. Some embodiments include a pharmaceutical composition comprising: (a) a safe and therapeutically effective amount of docetaxel or pharmaceutically acceptable salts thereof; (b) a safe and therapeutically effective amount of plinabulin; and (c) a pharmaceutically acceptable carrier, diluent, excipient or combination thereof.

In some embodiments, the pharmaceutical composition described herein can further include one or more pharmaceutically acceptable diluents. In some embodiments, the pharmaceutically acceptable diluent can include Kolliphor® (Polyethylene glycol (15)-hydroxystearate). In some embodiments, the pharmaceutically acceptable diluent can include propylene glycol. In some embodiments, the pharmaceutically acceptable diluents can include kolliphor (Kolliphor HS 15) and propylene glycol. In some embodiments, the pharmaceutically acceptable diluents can include kolliphor and propylene glycol, wherein the kolliphor is about 40% by weight and propylene glycol is about 60% by weight based on the total weight of the diluents. In some embodiments, the composition can further include one or more other pharmaceutically acceptable excipients.

Standard pharmaceutical formulation techniques can be used to make the pharmaceutical compositions described herein, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of Plinabulin or pharmaceutically acceptable salts thereof; and (b) a pharmaceutically acceptable carrier, diluent, excipient or combination thereof.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The compositions described herein are preferably provided in unit dosage form. As used herein, a "unit dosage form" is a composition containing an amount of a compound or composition that is suitable for administration to an animal, preferably a mammalian subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, although a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, sublingual, buccal, nasal, rectal, topical (including transdermal and intradermal), ocular, intracerebral, intracranial, intrathecal, intraarterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the activity of the compound or composition. The amount of carrier employed in conjunction with the compound or composition is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules (e.g., liquid gel capsule and solid gel capsule), granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, sucrose, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject composition is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium (EDTA), although other chelating agents may also be used in place or in conjunction with it.

For topical use, creams, ointments, gels, solutions or suspensions, etc., containing the composition disclosed herein are employed. Topical formulations may generally be comprised of a pharmaceutical carrier, co-solvent, emulsifier, penetration enhancer, preservative system, and emollient.

For intravenous administration, the compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of plinabulin described herein depends on the chemotherapeutic agent used; and on the condition to be treated; the selection of the appropriate dose is well within the knowledge of the skilled artisan. In some embodiments, a single dose of Plinabulin may be from about 5 mg/m$^2$ to about 150 mg/m$^2$ of body surface area, from about 5 mg/m$^2$ to about 100 mg/m$^2$ of body surface area, from about 10 mg/m$^2$ to about 100 mg/m$^2$ of body surface area, from about 10 mg/m$^2$ to about 80 mg/m$^2$ of body surface area, from about 10 mg/m$^2$ to about 50 mg/m$^2$ of body surface area, from about 10 mg/m$^2$ to about 40 mg/m$^2$ of body surface area, from about 10 mg/m$^2$ to about 30 mg/m$^2$ of body surface area, from about 13.5 mg/m$^2$ to about 100 mg/m$^2$ of body surface area, from about 13.5 mg/m$^2$ to about 80 mg/m$^2$ of body surface area, from about 13.5 mg/m$^2$ to about 50 mg/m$^2$ of body surface area, from about 13.5 mg/m$^2$ to about 40 mg/m$^2$ of body surface area, from about 13.5 mg/m$^2$ to about 30 mg/m$^2$ of body surface area, from about 15 mg/m$^2$ to about 80 mg/m$^2$ of body surface area, from about 15 mg/m$^2$ to about 50 mg/m$^2$ of body surface area, or from about 15 mg/m$^2$ to about 30 mg/m$^2$ of the body surface area. In some embodiments, a single dose of Plinabulin may be from about 13.5 mg/m$^2$ to about 30 mg/m$^2$ of body surface area. In some embodiments, a single dose of Plinabulin may be greater than about 5 mg/m$^2$, about 10 mg/m$^2$, about 12.5 mg/m$^2$, about 13.5 mg/m$^2$, about 15 mg/m$^2$, about 17.5 mg/m$^2$, about 20 mg/m$^2$, about 22.5 mg/m$^2$, about 25 mg/m$^2$, about 27.5 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, or about 100 mg/m$^2$, of the body surface area. In some embodiments, a single dose of Plinabulin may be less than about 5 mg/m$^2$, about 10 mg/m$^2$, about 12.5 mg/m$^2$, about 13.5 mg/m$^2$, about 15 mg/m$^2$, about 17.5 mg/m$^2$, about 20 mg/m$^2$, about 22.5 mg/m$^2$, about 25 mg/m$^2$, about 27.5 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, or about 100 mg/m$^2$, of body surface area. In some embodiments, a single dose of Plinabulin may be about 5 mg/m$^2$, about 10 mg/m$^2$, about 12.5 mg/m$^2$, about 13.5 mg/m$^2$, about 15 mg/m$^2$, about 17.5 mg/m$^2$, about 20 mg/m$^2$, about 22.5 mg/m$^2$, about 25 mg/m$^2$, about 27.5 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, or about 100 mg/m$^2$, of the body surface area.

Some embodiments relate to a composition comprising about 1 mg to 100 mg of plinabulin. In some embodiments, the composition includes about 5 mg to about 300 mg, from about 5 mg to about 200 mg, from about 7.5 mg to about 200 mg, from about 10 mg to about 100 mg, from about 15 mg to about 100 mg, from about 20 mg to about 100 mg, from about 30 mg to about 100 mg, from about 40 mg to about 100 mg, from about 10 mg to about 80 mg, from about 15 mg to about 80 mg, from about 20 mg to about 80 mg, from about 30 mg to about 80 mg, from about 40 mg to about 80 mg, from about 10 mg to about 60 mg, from about 15 mg to about 60 mg, from about 20 mg to about 60 mg, from about 30 mg to about 60 mg, or from about 40 mg to about 60 mg of plinabulin. In some embodiments, a single dose of Plinabulin or other therapeutic agent may be from about 20 mg to about 60 mg, from about 27 mg to about 60 mg, from about 20 mg to about 45 mg, or from about 27 mg to about 45 mg. In some embodiments, a single dose of Plinabulin or other therapeutic agent may be greater than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg. In some embodiments, a single dose of Plinabulin or other therapeutic agent may be less than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg.

Some embodiments relate to a pharmaceutical composition including plinabulin and one or more G-CSF drug.

Some embodiments relate to a sterile container comprising the pharmaceutical composition of plinabulin described herein.

Some embodiments include a kit comprising a plinabulin and docetaxel. In one embodiment, both plinabulin and docetaxel are provided in two separate sterile container. In the case of solids for reconstitution, the agents may be added to the container simultaneously or may be dry-powder filled into the container in two separate steps. In some embodiments, the solids are sterile crystalline products. In other embodiment, the solids are lyophiles.

EXAMPLE

Example 1

A multicenter, double-blind, randomized phase 2 study is performed to study the effect of plinabulin against neutropenia.

All patients receive docetaxel at a dose of 75 mg/m$^2$. Patients only with advanced or metastatic NSCLC after failing platinum therapy are enrolled. The eligibility of all patients are determined during a 28-day screening period.

Approximately 40 patients with advanced and metastatic NSCLC are enrolled. Patients are randomly assigned, with 10 patients enrolled in each arm, with the arm designation and planned intervention as follows:

Arm 1: Docetaxel (75 mg/m$^2$)+pegfilgrastim (6 mg)+placebo matching plinabulin

Arm 2: Docetaxel (75 mg/m$^2$)+plinabulin (20 mg/m$^2$)+placebo matching pegfilgrastim Arm 3: Docetaxel (75 mg/m$^2$)+plinabulin (10 mg/m$^2$)+placebo matching pegfilgrastim Arm 4: Docetaxel (75 mg/m$^2$)+plinabulin (5 mg/m$^2$)+placebo matching pegfilgrastim PK and PD analysis are performed to determine a dose that is most effective in reducing neutropenia ("recommended phase 3 dose" or "RP3D"). The PK/PD analysis can be done at the time 40 patients have completed at least Cycle 1.

Cycles 1 to 4 consist of docetaxel 75 mg/m$^2$ administered by IV infusion on Day 1 over 60 minutes every 21 days. On Day 1 of each cycle, patients get a single dose of plinabulin or placebo intravenously over 30 minutes (±5 minutes) in a double blinded manner 60 minutes post dose docetaxel infusion. On Day 2 of each cycle ≥24 hours after completing chemotherapy, all patients receive a single dose of pegfilgrastim (6 mg) or placebo (subcutaneous injection) in a double blinded manner.

If a chemotherapy cycle is delayed by more than 3 weeks, the patient will be withdrawn from the study. If a critical adverse event occurs during the cycle, the dosage of docetaxel may be reduced 20% in the next cycle. Only 1 docetaxel dose reduction is allowed. No dose reductions are allowed with plinabulin or pegfilgrastim.

If an increase in systolic blood pressure to >160 mmHg is observed after administration of plinabulin or placebo, oral amlodipine 10 mg or an equivalent calcium channel blocker should be administered before each dose subsequent. Increases in systolic blood pressure above 200 mmHg should be managed with nitroprusside or similar regimen per institutional practice. If hypertension can be successfully managed, patient can continue in the study at the discretion of the investigator.

To assess duration of severe neutropenia (DSN) in treatment Cycle 1 in patients treated with docetaxel (75 mg/m$^2$)+plinabulin (5, 10 or 20 mg/m$^2$) or with docetaxel (75 mg/m$^2$)+pegfilgrastim (6 mg) with matching placebos, neutrophils count are assessed at baseline; Pre-dose during Cycle 1, Day 1, 2, 5, 6, 7, 8, 9, 10, 15.

To assess the safety pharmacodynamics, the blood pressure is measured semi-continuously with 15 minutes intervals, starting 15 minutes pre-dose and lasting 6 hours after start of infusion with plinabulin or placebo.

CD34+ at baseline, Days 2, 5, and 8 in Cycle 1 and Day 1 in Cycle 2 are also measured.

After the completion of phase 2 study, a PK/PD analysis can also be conducted, using PK parameters of plinabulin and docetaxel, and the PD parameters of blood pressure and DSN in all patients receiving plinabulin or docetaxel. This analysis can determine the recommended phase 3 dose (RP3D) of plinabulin.

In addition, to assess duration of severe neutropenia (DSN) in treatment Cycle 1 in patients treated with docetaxel (75 mg/m$^2$)+plinabulin (5, 10 or 20 mg/m$^2$) or with docetaxel (75 mg/m$^2$)+pegfilgrastim (6 mg) with matching placebos, the Jonckheere-Terpstra Test for Ordered Alternatives (Hollander, Wolfe, and Chicken 2013) can be used. With this statistical procedure, the null hypothesis of equality among treatment group means can be tested ($\mu_j$'s, j=1, 2, 3, 4)

H0: µ1=µ2=µ3=µ4 against the alternative in which order is specified

H1: µ1≥µ2≥µ3≥µ4, where at least one of the inequalities is strict. The mean indices have the following interpretation: 1=docetaxel (75 mg/m$^2$)+pegfilgrastim (6 mg), 2=docetaxel (75 mg/m$^2$)+plinabulin (5 mg/m$^2$), 3=docetaxel (75 mg/m$^2$)+plinabulin (10 mg/m$^2$), and 4=docetaxel (75 mg/m$^2$)+plinabulin (20 mg/m$^2$).

Patients receive treatment with study drug for up to 4 cycles in this study, a treatment cycle is 21 days; thereafter, patients may continue receiving docetaxel and pegfilgrastim. After completion of 4 cycles, patients will complete a safety follow-up visit 30 days (±7 days) after end of treatment visit.

Treatment up to 4 cycles of study drug in this study will continue until any 1 of the following occurs: Dose limiting toxicity as defined in the docetaxel package insert; need for a protocol-prohibited dose reduction or study drug delay greater than 21 days; initiation of a protocol-prohibited concomitant medication or non-protocol chemo/biological therapy for treatment of his or her disease; development of a AE/SAE, illness, or condition that may interfere with the patient's participation or require treatment discontinuation; investigator opinion.

Patients may be pre-medicated with oral corticosteroids such as dexamethasone 16 mg per day (e.g., 8 mg bid) for 3 days starting 1 day prior to docetaxel administration in order to reduce the incidence and severity of fluid retention as well as the severity of hypersensitivity reactions.

Corticosteroids (except as described for premedication) and non-steroidal anti-inflammatory drugs (NSAIDs) may be prohibited except for the treatment of AEs and as pre-medication.

The use of strong CYP3A4 inhibitors as concomitant medications may be prohibited because docetaxel exposure increases by approximately 2-fold with the use of strong CYP3A4 inhibitors.

No anti-emetic pre-medication may be routinely administered for either treatment regimen. All attempts should be made to refrain from administering anti-emetics at baseline, predose and postdose Day 1 until completion of the triplicate ECGs on Day 1 in Cycle 1 in Phase 2. Ondansetron and other 5HT3 inhibitors are prohibited until the time that the scheduled triplicate ECGs are completed, due to their interference with the QTc study. After completion of the triplicate ECGs on Day 1 in Cycle 1, anti-emetics may be prescribed if indicated. In the event that anti-emetics will be required on Day 1 in Cycle 1, palonosetron should be given, and if that is not available, granisetron could be given. The use of anti-emetics should be recorded.

Patients who have FN should receive antibiotics per standard of care. The use of granulocyte colony-stimulating factor (G-CSF) as a treatment option during hospitalization for FN is strongly discouraged, since G-CSF is not approved for the treatment of FN, and is not likely to be effective. If, however, G-CSF treatment for FN is considered, the Investigator should contact the Medical Monitor prior to its use. The use of G-CSF may cause the patient to be unblinded and discontinued from the study. FN is defined as single temperature ≥38.3° C. orally or ≥38.0° C. over 1 hour; neutropenia <500 neutrophils/mcL or <1000 neutrophils/mcL and a predicted decline to ≤500/neutrophils/mcL over the next 48 hours (NCCN guidelines).

All patients have samples taken on Day 1 of plinabulin infusion.

TABLE 2

Plinabulin Sampling Schedule

|  | Pre-dose (immediately before infusion, up to 1 hour window) | End-of infusion (+5 minutes window) | Post-dose 30 minutes (+5 minutes window) | Post-dose 6.0 hours (+15 minutes window) |
|---|---|---|---|---|
| Cycle 1 |  |  |  |  |
| Day 1 | yes | yes | yes | yes |

All patients have samples taken on Day 1 of docetaxel.

TABLE 3

Docetaxel Sampling Schedule

|  | Pre-dose (immediately before infusion, up to 1 hour window) | End-of infusion (+5 minutes window) | Post-dose 30 minutes (+5 minutes window) | Post-dose 6.0 hours (+15 minutes window) |
|---|---|---|---|---|
| Cycle 1 |  |  |  |  |
| Day 1 | yes | yes | yes | yes |

All safety assessments used in this study are standard, i.e., widely used and generally recognized as reliable, accurate, and relevant, either in clinical practice or specifically in cancer patients. Questionnaires for bone pain and health-related QoL questionnaire evaluated with EORTC QLQ-C30 and EQ-5D-5L are validated for use in this population.

Example 2

A phase 3 study is conducted using the RP3D determined in the phase 2 study. Approximately 170 patients with one of the following diagnoses can be enrolled: advanced or metastatic breast cancer, who have failed ≥1 but <5 prior lines of chemotherapy; advanced or metastatic non-small cell lung cancer (NSCLC) after failing platinum therapy; or hormone refractory (androgen independent) metastatic prostate cancer. The RP3D obtained from Example 1 is used in this study. Approximately 130 patients are enrolled in the phase 3 study. Each eligible patient is stratified according to his or her diagnosis (advanced or metastatic breast cancer, NSCLC, or HRPC). Patients are randomly assigned with equal probability (1:1 ratio) or 65:65, with the arm designation and planned intervention as follows:

Arm 1: Docetaxel (75 mg/m$^2$)+pegfilgrastim (6 mg)+placebo matching plinabulin

Arm 2: Docetaxel (75 mg/m$^2$)+plinabulin (RP3D from Experiment 2)+placebo matching pegfilgrastim Data from all patients receiving the RP3D obtained in Example 1 are pooled for assessing the primary and secondary study endpoints.

Cycles 1 to 4 consist of docetaxel 75 mg/m$^2$ administered by IV infusion on Day 1 over 60 minutes every 21 days. On Day 1 of each cycle, patients get a single dose of plinabulin or placebo intravenously over 30 minutes (±5 minutes) in a double blinded manner 60 minutes postdose docetaxel infusion. On Day 2 of each cycle ≥24 hours after completing chemotherapy, all patients receive a single dose of pegfilgrastim (6 mg) or placebo (subcutaneous injection) in a double blinded manner.

If a chemotherapy cycle is delayed by more than 3 weeks, the patient will be withdrawn from the study. If a critical adverse event occurs during the cycle, the dosage of docetaxel may be reduced 20% in the next cycle. Only 1 docetaxel dose reduction is allowed. No dose reductions are allowed with plinabulin or pegfilgrastim.

If an increase in systolic blood pressure to >160 mmHg is observed after administration of plinabulin or placebo, oral amlodipine 10 mg or an equivalent calcium channel blocker should be administered before each dose subsequent. Increases in systolic blood pressure above 200 mmHg should be managed with nitroprusside or similar regimen per institutional practice. If hypertension can be successfully managed, patient can continue in the study at the discretion of the investigator.

All patients, including patients who withdraw from the study early, complete a safety follow-up visit 30 days (±7 days) after the last dose of study drug. Follow-up visits are required to monitor for ongoing treatment-related AEs. Laboratory test results (hematology and serum chemistry) are collected via a central laboratory. Urinalysis is performed at baseline only. CD34+ counts are established through a fluorescence-activated cell sorting (FACS) method.

To compare the duration of severe neutropenia (DSN) in treatment Cycle 1 in patients with advanced or metastatic breast cancer, who have failed ≥1 but <5 prior lines of chemotherapy; advanced or metastatic non-small cell lung cancer (NSCLC) after failing platinum therapy; or hormone refractory (androgen independent) metastatic prostate cancer treated with docetaxel (75 mg/m$^2$)+plinabulin (RP3D) versus docetaxel (75 mg/m$^2$)+pegfilgrastim (6 mg), neutrophils count is assessed at baseline; Pre-dose during Cycle 1, Day 1, 2, 5, 6, 7, 8, 9, 10, 15.

To assess between docetaxel (75 mg/m$^2$)+plinabulin (RP3D) versus docetaxel (75 mg/m$^2$)+pegfilgrastim (6 mg) in patients with advanced or metastatic breast cancer, who have failed ≥1 but <5 prior lines of chemotherapy; advanced or metastatic NSCLC after failing platinum therapy; or hormone refractory (androgen independent) metastatic prostate cancer, the following parameters are determined:

1) Incidence of Grade 4 neutropenia (absolute neutrophil count [ANC]<0.5×10$^9$/L) on Days 8 and 15 in Cycles 1 to 4
2) Incidence of febrile neutropenia (FN) (ANC<0.5× 10$^9$/L and body temperature ≥38.3° C.) in Cycles 1 to 4
3) Neutrophil nadir during Cycle 1
4) Incidence of documented infections in Cycles 1 to 4
5) Incidence and duration of hospitalizations due to FN in Cycles 1 to 4
6) Health-related Quality of Life (QoL)
7) Use of pegfilgrastim or filgrastim as treatment with neutropenia
8) Incidence of antibiotic use
9) Incidence of docetaxel dose delay, dose reduction, and/or dose discontinuation To determine the safety profile of the treatment, the following parameters are measured:

1) Incidence, occurrence, and severity of adverse events (AEs)/serious adverse events (SAEs)
2) Incidence, occurrence and severity of bone pain
3) Systemic tolerance (physical examination and safety laboratory assessments)

If a chemotherapy cycle is delayed by more than 3 weeks, the patient will be withdrawn from the study. If a critical adverse event occurs during the cycle, the dosage of docetaxel may be reduced 20% in the next cycle. Only 1 docetaxel dose reduction is allowed. No dose reductions are allowed with plinabulin or pegfilgrastim.

If an increase in systolic blood pressure to >160 mmHg is observed after administration of plinabulin or placebo, oral amlodipine 10 mg or an equivalent calcium channel blocker should be administered before each dose subsequent. Increases in systolic blood pressure above 200 mmHg should be managed with nitroprusside or similar regimen per institutional practice. If hypertension can be successfully managed, patient can continue in the study at the discretion of the investigator.

Patients should be pre-medicated with oral corticosteroids such as dexamethasone 16 mg per day (e.g., 8 mg bid) for 3 days starting 1 day prior to docetaxel administration in order to reduce the incidence and severity of fluid retention as well as the severity of hypersensitivity reactions (refer to Taxotere® Package Insert). For hormone-refractory metastatic prostate cancer, given the concurrent use of prednisone, the recommended premedication regimen is oral dexamethasone 8 mg, at 12 hours, 3 hours and 1 hour before the docetaxel infusion.

Example 3

DSN is obtained using the following methods (described below) for generation of ANC data and the observed neutrophil values on Day 8/Cycle 1 in the Phase 2 study. Day 8 neutrophil values measured in phase 2 study of Example 1 is shown to approximately coincide with the nadir of neutrophil counts after docetaxel treatment. The study may assume that the shape of the time/neutrophil recovery curve in plinabulin-treated patients is indistinguishable from the time/neutrophil recovery curve for filgrastim and its biosimilars.

In a study with filgrastim and its biosimilar, time course of ANC in Cycle 1 for the Per Protocol dataset can be found in the study described in Blackwell et al, *Annals of Oncology* 26: 1948-1953, 2015, which is incorporated herein by reference for this purpose in its entirety. Mean values and standard deviations of ANC during the 21-day follow-up period can be obtained from the reference. A computer simulation program can be used to generate random ANC data that asymptotically has the same means and standard deviations for the 21-day follow-up period as the publication. The simulation would then also generate the projected number of days with severe neutropenia, (i.e., the DSN).

Deming regression can be used to calculate the linear relationship between simulated nadir and DSN. The rank correlation between simulated nadir and DSN can be used to calculate the DSN with plinabulin (+docetaxel) and docetaxel alone. In the study, neutrophil counts are obtained on Day 8, which approximately coincides with the time that the neutrophil nadir occurs after docetaxel administration. The observed Day 8 neutrophil (nadir) values are computed into the linear relationship (Deming regression), mentioned above to calculate DSN for each patient. Using these methods, calculated mean DSN is 0.065 days for the plinabulin+ docetaxel arm, and 1.076 days for the docetaxel alone. Based on data with filgrastim in patients receiving docetaxel (Alexopoulos K et al, Cancer Chemother Pharmacol 1999, 43: 257-262), the assumption is that Grade 4 neutropenia in Cycle 1 would occur in a 2 times higher frequency with G-CSF+docetaxel versus plinabulin+docetaxel, resulting in a presumed mean DSN of 0.13 days for the G-CSF+ docetaxel combination.

The study may utilize a difference (arm 2 minus arm 1) of 0.65 days (non-inferiority margin) in DSN in Cycle 1 as the largest acceptable difference between plinabulin and pegfilgrastim. The non-inferiority test can evaluate the null hypothesis $H_0$: true difference (arm 2 minus arm 1) ≥0.65 against the alternative hypothesis $H_1$: true difference (arm 2 minus arm 1) <0.65. Plinabulin can be considered non-inferior to pegfilgrastim if in Cycle 1, the upper limit of the 2-sided 95% confidence interval for the true difference in mean duration of Grade 4 neutropenia is <0.65 days. A sample size of patients is based on sample size considerations as outlined.

Data suggest that FN is correlated with DSN. The frequency of FN with docetaxel monotherapy (100 mg/m$^2$)+ G-CSF is reported to be 1% in Cycle 1. FN frequency in Cycle 1 with docetaxel combined with doxorubicin and G-CSF is ~3%, which would translate into a DSN of 1 day according to Holmes Fa, et al; J Clin. Oncol. 2002; 20:727-731. Based on these data, it is assumed that the median DSN for docetaxel monotherapy+G-CSF wan be approximately 1 day.

The frequency of FN with docetaxel monotherapy (without G-CSF) is 11% in Cycle 1 (17% over all cycles) docetaxel dose of 100 mg/m$^2$ and 19.8% over all cycles at a lower docetaxel dose of 60 mg/m$^2$. The FN percentage is about 12.7% with 75 mg/m$^2$ docetaxel. Based on this range of FN and the relationship established between FN and DSN, the assumption is that, with docetaxel monotherapy at a dose of 75 mg/m$^2$ without G-CSF, the median DSN is estimated to be 4-5 days.

The margin can be selected based on the data that Taxotere/Adriamycin/cyclophosphamide (TAC) chemotherapy can induce a median DSN of 7 days in breast cancer patients receiving no G-CSF treatment, while G-CSF treatment reduces the mean DSN for this chemotherapy to 1.4 days (95% CI: 1.07-1.69) as shown in pegfilgrastim Study. Based on this a non-inferiority limit of 1 day is derived.

Based on the data and calculation, a non-inferiority margin of 0.65 would be reasonable and correspond to approximately a median of 4.5 days of DSN, as a ratio of 1 day to 7 days of DSN in the Zarxio® briefing document. A non-inferiority margin of 0.65 days can also be justified, because a difference of 0.65 days is not considered to be clinically meaningful.

The primary endpoint can be analyzed using an exact ţ-test. For endpoints other than Grade 4 neutropenia, analyses can be based on conventional methods (i.e., assuming asymptotic normality) for calculating 95% confidence intervals (CIs) and hypothesis testing. ANC nadir, a secondary endpoint, can be analyzed using the Wilcoxon rank sum test. Continuous variables and proportions can be analyzed using exact t-tests. Categorical data can be analyzed using non-parametric statistical methods.

For the exploratory analysis, continuous variables and proportions will be analyzed using exact t-tests. Categorical data will be analyzed using non-parametric statistical methods.

For the safety analysis, continuous variables and proportions will be analyzed using exact t-tests. Categorical data will be analyzed using non-parametric statistical methods.

Example 4

A randomized, double blind study to evaluate duration of severe neutropenia with plinabulin versus pegfilgrastim in patients with solid tumors receiving docetaxel myelosuppressive chemotherapy was performed. Patients were randomly assigned to the following arms (with the respective sample sizes): Arm 1: Docetaxel (75 mg/m$^2$)+Pegfilgrastim (6 mg) (n=14); Arm 2: Docetaxel (75 mg/m$^2$)+Plinabulin (20 mg/m$^2$) (n=14); Arm 3: Docetaxel (75 mg/m$^2$)+Plinabulin (10 mg/m$^2$) (n=14); and Arm 4: Docetaxel (75 mg/m$^2$)+ Plinabulin (5 mg/m$^2$) (n=13). The testing results are shown in FIG. 1 and Table 4.

TABLE 4

| Topline Neutropenia Data in Phase 2 Portion | | | | |
|---|---|---|---|---|
| Neutropenia | Neulasta 6 mg N = 14 | Plinabulin 5 mg/m2 N = 14 | Plinabulin 10 mg/m2 N = 14 | Plinabulin 20 mg/m2 N=13 |
| Grade 4 Incidence (%) | 14% | 23% | 21% | 15% |
| DSN (Days) | 0.14 | 0.46 | 0.43 | 0.38 |

As shown in FIG. 1, the neutrophil count in the pegfilgrastim group had an initial increase and then began to drop after 10 days, while the neutrophil count in the plinabulin groups started to rise again on day 10. The results showed that plinabulin was effective in treating neutropenia induced by chemotherapeutic agent. Plinabulin and Pegfilgrastim had different profile of reducing neutropenia, and the nadir timepoint was different for plinabulin versus pegfilgrastim, suggesting the two drugs can be used in combination to maintain the neutrophil count level continuously. The results also suggested that the amount of G-CSF drug or plinabulin required for the neutropenia treatment can be decreased due to the supplemental function of the combination.

Example 5

A multicenter, randomized study, with Phase 2 and Phase 3 portions is performed. The Phase 2 portion is randomized and open label. The selection of the plinabulin RP3D dose is based on impartial measures from PK and PD assessments, these assessments are not influenced by the open label design. The decision to complete the Phase 2 portion of the study as open label was made to reduce the complexities of study conduct and to allow for the assessment, via QoL, of same-day plinabulin dosing (i.e on the day of chemotherapy dosing) versus next day dosing with G-CSF. The phase 3 portion is double blind. An estimated total of 180 patients with breast cancer can be enrolled in the Phase 2 and Phase 3 parts of this study. Patients are stratified by region (China and Japan vs rest of the world).

Patients receive up to 4 cycles of a docetaxel/doxorubicin/cyclophosphamide based chemotherapy regimen, every 3 weeks (21 days). On Day 1 of Cycle 1, all patients receive docetaxel (75 mg/m$^2$), doxorubicin (50 mg/m$^2$), and cyclophosphamide (500 mg/m$^2$)—Taxotere, Adriamycin and cyclophosphamide (TAC).

During Cycles 2 to 4, the doxorubicin component may be omitted at the discretion of the investigator, i.e., TC can be administered instead of TAC.

The eligibility of all patients is determined during a 28-day screening period.

Since plinabulin has demonstrated efficacy against docetaxel-induced neutropenia in humans, and since the beneficial effects of plinabulin also were demonstrated in non-clinical studies with the two other components of the TAC regimen, plinabulin is expected to ameliorate neutropenia induced by TAC. For that reason, the Phase 2 portion has a parallel design (i.e., the treatments are assigned to separate groups of patients).

Phase 2 (Open Label): In Phase 2, approximately 60 patients with breast cancer are enrolled. Patients are randomly assigned to one of the treatment arms, with approximately 20 patients enrolled in Arm 1 and 15 patients in each of Arm 2 to Arm 4, with the arm designation and planned intervention as follows: Arm 1: TAC+pegfilgrastim (6.0 mg); Arm 2: TAC+plinabulin (10 mg/m2); Arm 3: TAC+plinabulin (20 mg/m2); Arm 4: TAC+plinabulin (30 mg/m2). Table 5 below shows the treatment schedule for the different groups.

plinabulin over 30 minutes (±5 minutes), 30 minutes after the end of the TAC (or TC for Cycles 2 to 4) infusion on Day 1. On Day 2 of each cycle (≥24 hours after completing chemotherapy) patients in Arm 1 receive a single dose of pegfilgrastim (6.0 mg) (subcutaneous injection) in an open label treatment.

TABLE 5

Treatments Administered for Phase 2

|  | Cycles 1 to 4, Day 1 21 Day Cycle (TAC) | Cycles 1 to 4, Day 1 21 Day Cycle 30 (±2) minutes from the end of the Docetaxel infusion | Cycles 1 to 4, Day 2 21 Day Cycle ≥ 24 hours post Day 1 |
|---|---|---|---|
| Arm 1 | Pre-medication (up to 30 minutes) Doxorubicin (50 mg/m$^2$) = Approximately 15 minute IV treatment Cyclophosphamide (500 mg/m$^2$) = Approximately 30 minute IV treatment Docetaxel (75 mg/m$^2$) = Approximately 60 minute IV treatment | No drug administered | Pegfilgrastim (6.0 mg) SC single dose |
| Arm 2 | Pre-medication (up to 30 minutes) Doxorubicin (50 mg/m$^2$) = Approximately 15 minute IV treatment Cyclophosphamide (500 mg/m$^2$) = Approximately 30 minute IV treatment Docetaxel (75 mg/m$^2$) = Approximately 60 minute IV treatment | Plinabulin (10 mg/m$^2$) 30 minute IV infusion | No drug administered |
| Arm 3 | Pre-medication (up to 30 minutes) Doxorubicin (50 mg/m$^2$) = Approximately 15 minute IV treatment Cyclophosphamide (500 mg/m$^2$) = Approximately 30 minute IV treatment Docetaxel (75 mg/m$^2$) = Approximately 60 minute IV treatment | Plinabulin (20 mg/m$^2$) 30 minute IV infusion | No drug administered |
| Arm 4 | Pre-medication (up to 30 minutes) Doxorubicin (50 mg/m$^2$) = Approximately 15 minute IV treatment Cyclophosphamide (500 mg/m$^2$) = Approximately 30 minute IV treatment Docetaxel (75 mg/m$^2$) = Approximately 60 minute IV treatment | Plinabulin (30 mg/m$^2$) 60 minute IV infusion | No drug administered |

Abbreviations: IV = intravenous; SC = subcutaneous
Note:
During Cycles 2 to 4, the doxorubicin component may be omitted at the discretion of the investigator, i.e., TC will be administered instead of TAC.

In addition, approximately 30 patients with breast cancer are enrolled: Once approximately 18 patients have been randomized to receive TAC (or TC for Cycles 2 to 4)+monotherapy plinabulin in each of Arms 2, 3, and 4, approximately 10 additional patients are enrolled per arm to receive the same TAC (or TC for Cycles 2 to 4) and plinabulin treatment+pegfilgrastim (6.0 mg). Patients are randomly assigned to one of the following treatment arms:

TAC+plinabulin (10 mg/m2)+pegfilgrastim (6.0 mg)
TAC+plinabulin (20 mg/m2)+pegfilgrastim (6.0 mg)
TAC+plinabulin (30 mg/m2)+pegfilgrastim (6.0 mg)

The patients in the exploratory safety evaluation follow the same schedule as patients receiving TAC and monotherapy plinabulin in Arms 2, 3, and 4.

The study can be temporarily closed to enrollment when a total of 60 patients have been enrolled and completed at least 1 treatment cycle in each arm in Phase 2. Once the study is temporarily closed to enrollment in Phase 2, a PK/PD analysis is performed to determine the RP3D. The PK/PD analysis is done by an independent party at the time 60 patients in Phase 2 have completed at least Cycle 1.

In Phase 2 (Open Label), Cycles 1 to 4 consist of TAC (or TC for Cycles 2 to 4) administered IV on Day 1, every 21 days. Patients in Arms 2 and 3 receive a single dose of For exploratory PK/PD purposes, the following arms are added with approximately 10 patients per arm: TAC+plinabulin (10 mg/m2)+pegfilgrastim (6.0 mg); TAC+plinabulin (20 mg/m2)+pegfilgrastim (6.0 mg); TAC+plinabulin (30 mg/m2)+pegfilgrastim (6.0 mg)

Phase 3 (Double Blind): Phase 3 does not begin until RP3D has been determined based on the Phase 2 PK/PD analysis as mentioned above; the RP3D is the only plinabulin dose administered in Phase 3.

In Phase 3, approximately 120 patients with breast cancer can be enrolled. Patients are randomly assigned to one of the treatment arms, with approximately 60 patients enrolled in each arm, with the arm designation and planned intervention as follows: Arm 1: TAC+pegfilgrastim (6.0 mg)+placebo matching plinabulin; Arm 2: TAC+plinabulin (RP3D)+placebo matching pegfilgrastim.

In Phase 3 (double blinded treatment), Cycles 1 to 4 consist of TAC (or TC for Cycles 2 to 4) administered IV on Day 1, every 21 days. Patients receive a single dose of plinabulin or placebo IV over 30 minutes (±5 minutes) in a double blinded manner, 30 minutes after the end of the TAC (or TC for Cycles 2 to 4) infusion. On Day 2 of each cycle (≥24 hours after completing chemotherapy) all patients receive a single dose of pegfilgrastim (6.0 mg) or placebo (subcutaneous injection) in a double blinded manner.

Plinabulin or Matching Placebo: Plinabulin is administered at a dose of 10, 20, or 30 mg/m2. For Phase 3, matching placebo is administered in an equal volume.

Pegfilgrastim or Matching Placebo: Pegfilgrastim is administered at a dose of 6 mg as a single dose syringe. For Phase 3, matching placebo is administered in an equal volume.

The recommended dosage of pegfilgrastim is a single subcutaneous injection of 6.0 mg administered once per chemotherapy cycle in adults. Pegfilgrastim is not administered between 14 days before and 24 hours after administration of cytotoxic chemotherapy.

Docetaxel: Docetaxel is administered at a dose of 75 mg/m2. Administration should be carried out with a 1-hour IV infusion per institutional protocol at the dose prescribed by this clinical study protocol (75 mg/m2). Dexamethasone (16 mg per day administered as 8 mg twice daily, or as per institution standard) is given on the day before, the day of (Day 1), and the day following docetaxel infusion (Day 2).

Doxorubicin: Doxorubicin is administered at a dose of 50 mg/m2. Doxorubicin is potentially cardiotoxic. Risk for doxorubicin cardiotoxicity increases with the cumulative lifetime dose of doxorubicin. At the doxorubicin dose and schedule in this study, patients receive a cumulative doxorubicin dose of 240 mg/m2 of body surface area, below the threshold for symptomatic cardiac dysfunction. Patients should be monitored, per institutional standard, for doxorubicin cardiotoxicity.

During Cycles 2 to 4, the doxorubicin component may be omitted at the discretion of the investigator, i.e., TC can be administered instead of TAC.

Cyclophosphamide: Cyclophosphamide is administered at a dose of 500 mg/m2.

TAC Regimen: All patients received 3 week cycles of TAC chemotherapy. In each cycle, doxorubicin (50 mg/m2) given as a 15-minute IV infusion is administered first, followed immediately by cyclophosphamide (500 mg/m2) given as a 30-minute IV infusion, and then by docetaxel (75 mg/m2) administered as 1-hour IV infusion (the infusion times stated are approximate). Patients receiving TAC chemotherapy as an adjuvant treatment for their early breast cancer, should receive 4 cycles of TAC chemotherapy and at the discretion of the investigator up to 6 cycles of TAC chemotherapy (i.e., after completion of the 4 cycles on the protocol, these patients continue to receive TAC chemotherapy but with open label pegfilgrastim to prevent neutropenia).

TAC has a high risk (>20%) of causing FN. The NCCN guidelines recommend routine, primary prophylaxis with myeloid growth factor support in the treatment patients with high risk regimens such as TAC. During Cycles 2 to 4, the doxorubicin component may be omitted at the discretion of the investigator, i.e., TC may be administered instead of TAC.

Dose Interruptions and Modifications: All AEs should be assessed according to the CTCAE, v4.03. In event of multiple toxicities, dose delays and modifications should occur in accordance with the highest AEs observed.

No dose reductions are allowed with plinabulin or pegfilgrastim.

All patients, including patients who withdraw from the study early, complete a safety follow-up visit 28 days (±7 days) after the last dose of study drug. If, in the opinion of the investigator, the patient benefit from more than 4 cycles of TAC (or TC), then the fifth cycle does not start until completion of the safety follow-up visit (in this instance, the safety follow up visit is Cycle 4 Day 21). Follow-up visits are required to monitor for ongoing treatment-related AEs. All patients experiencing drug-related toxicities of Grade ≥2 at the End of Treatment (EOT) visit should be followed-up at least monthly until the AE(s) resolves to Grade ≤1, the event is considered to be chronic, or the patient receives other anti-cancer therapy. The method of follow-up assessment is at the Investigator's discretion (for example, patient site visit or telephone call).

Laboratory test samples (hematology and serum chemistry) are collected and sent to the protocol central laboratory. Safety laboratory tests are required prior to treatment on Day 1 of each cycle and can be collected by a local laboratory; however, all other scheduled blood samples as per the schedule assessments and procedure table must also be obtained for central laboratory assessment. Urinalysis is performed at screening (and at other time points if clinically indicated). CD34+ counts is measured through a fluorescence-activated cell sorting (FACS) method.

All patients, including patients who withdraw from the study early, completes a safety follow-up visit 28 days (±7 days) after the last dose of study drug. Follow-up visits are required to monitor for ongoing treatment related AEs. All patients experiencing drug-related toxicities of Grade ≥2 at the EOT visit are followed-up at least monthly until the AE(s) resolves to Grade 1, the event is considered to be chronic, or the patient receives other anti-cancer therapy. The method of follow-up assessment is at the Investigator's discretion (for example, patient site visit or telephone call).

Patients continue treatment up to 4 cycles of study drug in this study, thereafter, patients may continue open label TAC (or TC) and open label pegfilgrastim at the investigator's discretion. Patients complete a safety follow-up visit 28 days (±7 days) after the last dose of study drug. If, in the opinion of the investigator, the patient will benefit from more than 4 cycles of TAC (or TC), then the fifth cycle will not start until completion of the safety follow-up visit (in this instance, the safety follow up visit will be Cycle 4 Day 21).

Treatment up to 4 cycles of study drug in this study can continue until any 1 of the following occurs: Drug related AEs as described in the TAC package inserts which either prevent further dosing or cause dose delays of TAC chemotherapy greater than 21 days (see docetaxel, doxorubicin and cyclophosphamide package inserts); need for a protocol-prohibited dose reduction or study drug delay greater than 21 days; initiation of a protocol-prohibited concomitant medication or non-protocol chemo/biological therapy for treatment of their disease; development of a SAE/AE, illness or condition that may interfere with the patient's participation or require treatment discontinuation; Investigator opinion; Sponsor decision; or Voluntary withdrawal of consent.

The occurrence of specific Grade 3 or 4 AEs during chemotherapy requires a dose reduction, delay, or discontinuation. If a critical AE occurs during chemotherapy, the dosage of TAC may be reduced or modified as per the package inserts (docetaxel Package Insert, doxorubicin package insert, and cyclophosphamide Package Insert). On dosing days when the patients have an active infection, this must be treated adequately with antibiotics; administration with study drug must be withheld until the infection is resolved.

Dose Modification for TAC Chemotherapy: In the event a patient experiences an episode of FN or a documented infection, docetaxel should be reduced in subsequent cycles to 60 mg/m$^2$. If Grade 3 or 4 nausea, vomiting or diarrhea is experienced despite prophylactic therapy, doxorubicin is to be reduced to 40 mg/m$^2$ in subsequent cycles. For Grade 3 or 4 stomatitis, docetaxel is to be reduced to 60 mg/m$^2$ in subsequent cycles. If stomatitis still occurs after dose reducing docetaxel, doxorubicin is to be reduced to 40 mg/m² in subsequent cycles. In the event of Grade 3 or 4 neuropathy, the patient should be withdrawn from the study.

For other toxicities, treatment is held for a maximum of 2 weeks until recovery to Grade 1 and retreated for the subsequent cycle at a dose modified as appropriate to the toxicity. If treatment is held for more than 2 consecutive weeks, the patient can either be treated with docetaxel and cyclophosphamide only at the previous cycle doses (i.e., TC, omitting the doxorubicin) or removed from study treatment at the discretion of the investigator.

Pharmacokinetics: The population pharmacokinetics approach can be used to characterize the pharmacokinetics of plinabulin and TAC following doses of 10, 20, and 30 mg/m2 and TAC in Cycle 1 of the Phase 2 portion of the study. Pharmacodynamics Patients in Phase 2 participate in the PD assessments. The PD assessments include blood pressure and DSN in Cycle 1 of the Phase 2 portion of the study.

Treatment doses reduced for toxicity should not be re-escalated. During Cycles 2 to 4, the doxorubicin component may be omitted at the discretion of the investigator, i.e., TC is administered instead of TAC. Should a patient discontinue from the study during a treatment cycle, the patient continues to be monitored by their physician according to standard of care No dose reductions are allowed with plinabulin or pegfilgrastim. For patient or investigator convenience, or for administrative reasons (e.g. clinic closure for holidays), study drug administration for Cycles 2 to 4 can be adjusted by plus or minus 2 days.

Example 6

The combination of G-CSF (e.g., pegfilgrastim or filgrastim) and plinabulin is tested for its effect in reducing neutropenia induced by chemotherapy or radiation therapy. Patients having cancer receiving myelosuppresive chemotherapy or radiation therapy are assigned into the following groups: Arm (1) administration of a combination of G-CSF (e.g., pegfilgrastim or filgrastim) in the range of about 1 mg-25 mg (e.g., 0.1 mg-6 mg, 1 mg-5.5 mg, 2 mg-5.5 mg, 2 mg-4 mg, 3 mg-6 mg, 3 mg-5.5 mg, 4 mg-5.5 mg, or less than 6 mg) and plinabulin in the range of about 1 mg/m²-50 mg/m² (e.g., 1-20, 1-30, 5-10, 5-30, 5, 10, 20, 30 mg/m²); Arm (2) administration of G-CSF (e.g., pegfilgrastim or filgrastim) alone; Arm (3) administration of plinabulin alone; and Arm (4) administration of placebo.

Plinabulin or Matching Placebo: Plinabulin is administered at a selected dose ((e.g., 1-20, 1-30, 5-10, 5-30, 5, 10, 20, 30 mg/m²). In one control group, matching placebo is administered in an equal volume. Pegfilgrastim or Matching Placebo: Pegfilgrastim is administered subcutaneously at the selected dose (e.g., 0.1 mg-6 mg, 1 mg-5.5 mg, 2 mg-5.5 mg, 2 mg-4 mg, 3 mg-6 mg, 3 mg-5.5 mg, 4 mg-5.5 mg, or less than 6 mg) as a single dose syringe. In another control group, matching placebo is administered in an equal volume.

The population pharmacokinetics approach can be used to characterize the pharmacokinetics of plinabulin and pegfilgrastim following the administration of a chemotherapy or radiotherapy. The pharmacodynamics assessments include blood pressure and DSN in various cycles of the study.

It is expected that the combination of G-CSF (e.g., pegfilgrastim or filgrastim) and plinabulin is effective in reducing neutropenia, particularly severe grade 3/4 neutropenia and the combination can maintain the patient's neutrophil count to allow for continued chemotherapy treatment.

What is claimed is:

1. A method of treating docetaxel-induced neutropenia in a subject, comprising administering a single dose of plinabulin in a 21-day docetaxel treatment cycle and administering one or more G-CSF drugs.

2. The method of claim 1, wherein the amount of plinabulin in the single dose is greater than 1 mg/m² and less than 40 mg/m2.

3. The method of claim 1, wherein the plinabulin is administered less than 1 hour after the administration of docetaxel.

4. The method of claim 1, wherein the plinabulin is administered 10 minutes to 40 minutes after the administration of docetaxel.

5. A method of treating a Docetaxel, Doxorubicin, and Cyclophosphamide (TAC) or Docetaxel and Cyclophosphamide (TC) chemotherapy-induced neutropenia in a subject, comprising administering a single dose of plinabulin in a 21-day treatment cycle and administering one or more G-CSF drugs.

6. The method of claim 5, wherein the amount of plinabulin in the single dose is greater than 1 mg/m2 and less than 40 mg/m2.

7. The method of claim 5, wherein the plinabulin is administered less than 1 hour after the administration of the TAC or TC chemotherapy.

8. The method of claim 1, wherein the neutropenia is a grade 3 or 4 neutropenia.

9. The method of claim 1, comprising reducing an incidence of grade 4 neutropenia by at least 5%.

10. The method of claim 1, comprising reducing a duration of grade 4 neutropenia by at least 2 times.

11. A method of treating a chemotherapy induced neutropenia, comprising administering a single dose of plinabulin in a chemotherapy treatment cycle within 2 hours after the administration of the chemotherapy and administering one or more G-CSF drugs, wherein the dose of the G-CSF drug is in the range of 1 mg to 10 mg.

12. The method of claim 11, wherein the G-CSF drug is pegfilgrastim.

13. The method of claim 11, comprising administering the GCSF drug at least 24 hours after the administration of the chemotherapy.

14. The method of claim 11, comprising administering a single dose of plinabulin in a 21-day treatment cycle.

15. The method of claim 11, comprising administering plinabulin at a dose in the range of 1 mg/m² to 50 mg/m2.

16. The method of claim 1, wherein the patient has an advanced or metastatic breast cancer, early breast cancer, non-small cell lung cancer, or refractory metastatic prostate cancer.

17. The method of claim 1, wherein administering one or more G-CSF drugs is administered in a dose in a range from of 3 mg to 6 mg.

18. The method of claim 5, wherein administering one or more G-CSF drug is administered in a dose in a range from of 3 mg to 6 mg.

19. The method of claim 11, wherein the dose of the G-CSF drug is in a range from of 3 mg to 6 mg.

* * * * *

UNITED STATES PATENT AND TRADEMARK OFFICE
CERTIFICATE OF CORRECTION

PATENT NO. : 11,400,086 B2
APPLICATION NO. : 16/482547
DATED : August 2, 2022
INVENTOR(S) : Ramon Mohanlal It is certified that error appears in the above-identified patent and that said Letters Patent is hereby corrected as shown below:

On the Title Page

Page 3, Column 1 (Other Publications), Line 34, delete "Ariloxy" and insert -- Aryloxy --.

Page 3, Column 2 (Other Publications), Line 1, delete "thereapy:" and insert -- therapy: --.

Page 4, Column 1 (Other Publications), Line 9, delete "2/8(5340):" and insert -- 278(5340): --.

Page 4, Column 1 (Other Publications), Line 30, delete "(VCA)" and insert -- (VDA) --.

Page 4, Column 2 (Other Publications), Line 54, delete "2,5-Piperazinediones1a,"" and insert -- 2,5-Piperazinediones," --.

Page 4, Column 2 (Other Publications), Line 65, delete "eininge" and insert -- einige --.

Page 5, Column 1 (Other Publications), Line 1, delete "Kiketopiperazine" and insert -- Diketopiperazine --.

Page 5, Column 2 (Other Publications), Line 5, delete "antibody-antimocrotubule" and insert -- antibody-antimicrotubule --.

Page 5, Column 2 (Other Publications), Line 8, delete "[n" and insert -- In --.

Page 6, Column 1 (Other Publications), Line 23, delete "Qncology" and insert -- Oncology --.

Page 6, Column 1 (Other Publications), Line 24, delete "Purifiied" and insert -- Purified --.

Page 6, Column 2 (Other Publications), Line 4, delete "Plinabuilin" and insert -- Plinabulin --.

Page 7, Column 1 (Other Publications), Line 41, delete "Nucelotide" and insert -- Nucleotide --.

Signed and Sealed this
Twentieth Day of December, 2022

*Katherine Kelly Vidal*

Katherine Kelly Vidal
*Director of the United States Patent and Trademark Office*

CERTIFICATE OF CORRECTION (continued)
U.S. Pat. No. 11,400,086 B2

Page 7, Column 1 (Other Publications), Line 54, delete "Medicial Chemstry," and insert -- Medicinal Chemistry, --.

Page 7, Column 1 (Other Publications), Line 62, delete "I0" and insert -- IO --.

Page 7, Column 1 (Other Publications), Line 65, delete "doxorubiin," and insert -- doxorubicin, --.

Page 7, Column 2 (Other Publications), Line 27, delete "tubuline," and insert -- tubulin, --.

Page 7, Column 2 (Other Publications), Line 50, delete "Immunolog," and insert -- Immunology, --.

Page 7, Column 2 (Other Publications), Line 53, delete "mebrolizumag," and insert -- pembrolizumab, --.

In the Specification

Column 4, Line 67, delete "vaculitis" and insert -- vasculitis --.

Column 5, Line 26, delete "cyclosphosphamide," and insert -- cyclophosphamide, --.

Column 9, Line 2, delete "ifosfamine," and insert -- ifosfamide, --.

Column 9, Line 8, delete "irincotecan," and insert -- irinotecan, --.

Column 9, Line 9-10, delete "irincotecan/cisplatin," and insert -- irinotecan/cisplatin, --.

Column 9, Line 19, delete "ciaplatin/etoposide," and insert -- cisplatin/etoposide, --.

Column 9, Line 30, delete "irincotecan," and insert -- irinotecan, --.

Column 9, Line 54, delete "ifosfamine," and insert -- ifosfamide, --.

Column 9, Line 61, delete "irincotecan," and insert -- irinotecan, --.

Column 9, Line 62, delete "irincotecan/cisplatin," and insert -- irinotecan/cisplatin, --.

Column 10, Line 4, delete "ciaplatin/etoposide," and insert -- cisplatin/etoposide, --.

Column 10, Line 14 (approx.), delete "irincotecan," and insert -- irinotecan, --.

Column 25, Line 60, delete "36 g," and insert -- 36 h, --.

Column 26, Line 11, delete "embodiments" and insert -- embodiments. --.

Column 28, Line 25, delete "croscarmelose;" and insert -- croscarmellose; --.

Column 35, Line 52, delete "discontinuation" and insert -- discontinuation. --.

Column 35, Line 59, delete "assessments)" and insert -- assessments). --.

Column 40, Line 47 (approx.), delete "(6.0 mg)" and insert -- (6.0 mg). --.

Column 41, Line 33, delete "mg/m2." and insert -- mg/m$^2$. --.

Column 43, Line 38, delete "myelosuppresive" and insert -- myelosuppressive --.

In the Claims

Column 44, Line 11 (approx.), In Claim 2, delete "mg/m2." and insert -- mg/m$^2$. --.

Column 44, Line 27 (approx.), In Claim 6, delete "mg/m2." and insert -- mg/m$^2$. --.

Column 44, Line 51 (approx.), In Claim 15, delete "mg/m2." and insert -- mg/m$^2$. --.